US011499183B2

(12) United States Patent
Stumbo et al.

(10) Patent No.: US 11,499,183 B2
(45) Date of Patent: Nov. 15, 2022

(54) SYSTEM AND METHOD FOR DROPLET DETECTION

(71) Applicant: Bio-Rad Laboratories, Inc., Hercules, CA (US)

(72) Inventors: David P. Stumbo, Pleasanton, CA (US); George Carman, Livermore, CA (US); Steve Hobbs, Pleasanton, CA (US); Anthony J. Makarewicz, Jr., Livermore, CA (US); Dmitri Simonian, Mountain View, CA (US); David Glade, San Ramon, CA (US); Joshua Oen, Fremont, CA (US); Denis Pristinski, Pleasanton, CA (US); John Dzenitis, Danville, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 916 days.

(21) Appl. No.: 16/022,500

(22) Filed: Jun. 28, 2018

(65) Prior Publication Data

US 2019/0002956 A1    Jan. 3, 2019

Related U.S. Application Data

(60) Provisional application No. 62/526,259, filed on Jun. 28, 2017.

(51) Int. Cl.
*G01N 15/14* (2006.01)
*B01F 3/08* (2006.01)
(Continued)

(52) U.S. Cl.
CPC .............. *C12Q 1/686* (2013.01); *B01F 23/41* (2022.01); *B01L 3/502784* (2013.01);
(Continued)

(58) Field of Classification Search
None
See application file for complete search history.

(56) References Cited

U.S. PATENT DOCUMENTS 4,676,898 A    6/1987  Saxena
6,348,354 B1 *  2/2002  Adolfsen ............... G01N 35/08
                                                 422/105

(Continued)

FOREIGN PATENT DOCUMENTS

WO    2007011622 A2    1/2007
WO    2012081983 A1    6/2012

OTHER PUBLICATIONS

Young, Lee W., Authorized Officer, ISA / US, Commissioner for Patents, "International Search Report" in connection with related International Application No. PCT/US2018/040125, dated Nov. 6, 2018, 5 pages.

(Continued)

Primary Examiner — Brian R Gordon
(74) Attorney, Agent, or Firm — Kolisch Hartwell, P.C.

(57) ABSTRACT

Systems and methods for detection of a signal from droplets of an emulsion. An exemplary system may comprise a fluid transporter having a tube with an open end for aspirating droplets, a singulator to arrange the droplets in single file and to space the single-file droplets from one another, and a detection channel in optical communication with a detector configured to detect a signal from droplets. In some embodiments, the singulator may have a channel junction at which a stream of droplets in single file is combined with a stream of spacing fluid, and a tapered spacing channel extending downstream from the channel junction toward the detection channel. In some embodiments, the fluid transporter may suck droplet-containing fluid and spacing fluid through the detection channel from respective sources. In some embodi- (Continued)

ments, droplets may be subjected to a disaggregation routine before they are passed through the detection channel.

13 Claims, 11 Drawing Sheets

(51) Int. Cl.
| | | |
|---|---|---|
| *C12Q 1/6848* | (2018.01) | |
| *C12Q 1/6844* | (2018.01) | |
| *C12Q 1/686* | (2018.01) | |
| *B01L 3/00* | (2006.01) | |
| *C12Q 1/6851* | (2018.01) | |
| *B01F 23/41* | (2022.01) | |

(52) U.S. Cl.
CPC ......... *C12Q 1/6846* (2013.01); *C12Q 1/6848* (2013.01); *C12Q 1/6851* (2013.01); *G01N 15/1429* (2013.01); *G01N 15/1434* (2013.01); *G01N 15/1459* (2013.01); *B01L 3/502776* (2013.01); *B01L 2200/0673* (2013.01); *B01L 2300/0654* (2013.01); *G01N 2015/1481* (2013.01)

(56) References Cited

U.S. PATENT DOCUMENTS

| | | | |
|---|---|---|---|
| 6,641,993 B1* | 11/2003 | Jacobs | B01F 5/10 366/305 |
| 6,797,056 B2 | 9/2004 | David | |
| 7,294,503 B2 | 11/2007 | Quake et al. | |
| 7,641,862 B2 | 1/2010 | Noetzel et al. | |
| 7,772,287 B2* | 8/2010 | Higuchi | B01F 5/0478 516/21 |
| 8,241,571 B2 | 8/2012 | Goix et al. | |
| 9,132,394 B2 | 9/2015 | Makarewicz, Jr. et al. | |
| 2003/0040105 A1* | 2/2003 | Sklar | B01F 13/0071 435/287.2 |
| 2006/0072177 A1 | 4/2006 | Putnam et al. | |
| 2007/0117212 A1* | 5/2007 | Kautz | B01L 3/502784 436/137 |
| 2007/0231215 A1* | 10/2007 | Mototsu | B01L 3/0275 422/400 |
| 2008/0003142 A1 | 1/2008 | Link et al. | |
| 2008/0014589 A1 | 1/2008 | Link et al. | |
| 2009/0014360 A1 | 1/2009 | Toner et al. | |
| 2009/0056116 A1 | 3/2009 | Presley et al. | |
| 2009/0060793 A1* | 3/2009 | Eickhoff | G01N 35/10 422/400 |
| 2009/0202392 A1* | 8/2009 | Urano | B01L 3/0275 422/400 |
| 2010/0015606 A1 | 1/2010 | Davies et al. | |
| 2010/0078077 A1 | 4/2010 | Ismagilov et al. | |
| 2010/0173394 A1 | 7/2010 | Colston, Jr. et al. | |
| 2011/0311978 A1 | 12/2011 | Makarewicz, Jr. et al. | |
| 2012/0108721 A1 | 5/2012 | Mazutis | |
| 2012/0153185 A1* | 6/2012 | Ito | B01L 3/502776 356/338 |
| 2012/0190033 A1 | 7/2012 | Ness et al. | |
| 2013/0109575 A1* | 5/2013 | Kleinschmidt | G01N 1/38 506/2 |
| 2013/0236901 A1* | 9/2013 | Potier | C12Q 1/6806 435/6.12 |
| 2013/0295568 A1 | 11/2013 | Link | |
| 2014/0045712 A1 | 2/2014 | Link et al. | |
| 2014/0048458 A1* | 2/2014 | Ito | G01N 15/1459 209/577 |
| 2014/0071452 A1 | 3/2014 | Fleischer | |
| 2014/0170736 A1 | 6/2014 | Heredia et al. | |
| 2014/0200164 A1* | 7/2014 | Makarewicz, Jr. | B01L 3/502784 506/12 |
| 2014/0202546 A1 | 7/2014 | Ismagilov et al. | |
| 2014/0221239 A1 | 8/2014 | Carman et al. | |
| 2014/0251879 A1* | 9/2014 | Deshpande | B07C 5/02 209/577 |
| 2015/0065396 A1 | 3/2015 | Kiani et al. | |
| 2015/0204774 A1* | 7/2015 | Ito | G01N 15/147 209/644 |
| 2016/0051958 A1 | 2/2016 | Kung et al. | |
| 2016/0171686 A1 | 6/2016 | Du et al. | |
| 2016/0257992 A1 | 9/2016 | Tsukuda | |
| 2017/0007998 A1 | 1/2017 | Fraden et al. | |
| 2017/0183722 A1 | 6/2017 | Link | |
| 2019/0126277 A1 | 5/2019 | Hung et al. | |
| 2020/0108393 A1 | 4/2020 | Lee et al. | |

OTHER PUBLICATIONS

Young, Lee W., Authorized Officer, ISA / US, Commissioner for Patents, "Written Opinion of the International Searching Authority" in connection with related International Application No. PCT/US2018/040125, dated Nov. 6, 2018, 8 pages.

Viskanic, Martino, Examiner, European Patent Office, "Extended European Search Report" in connection with related European Patent App. No. 18823895.0, dated Jan. 26, 2021, 8 pgs.

* cited by examiner

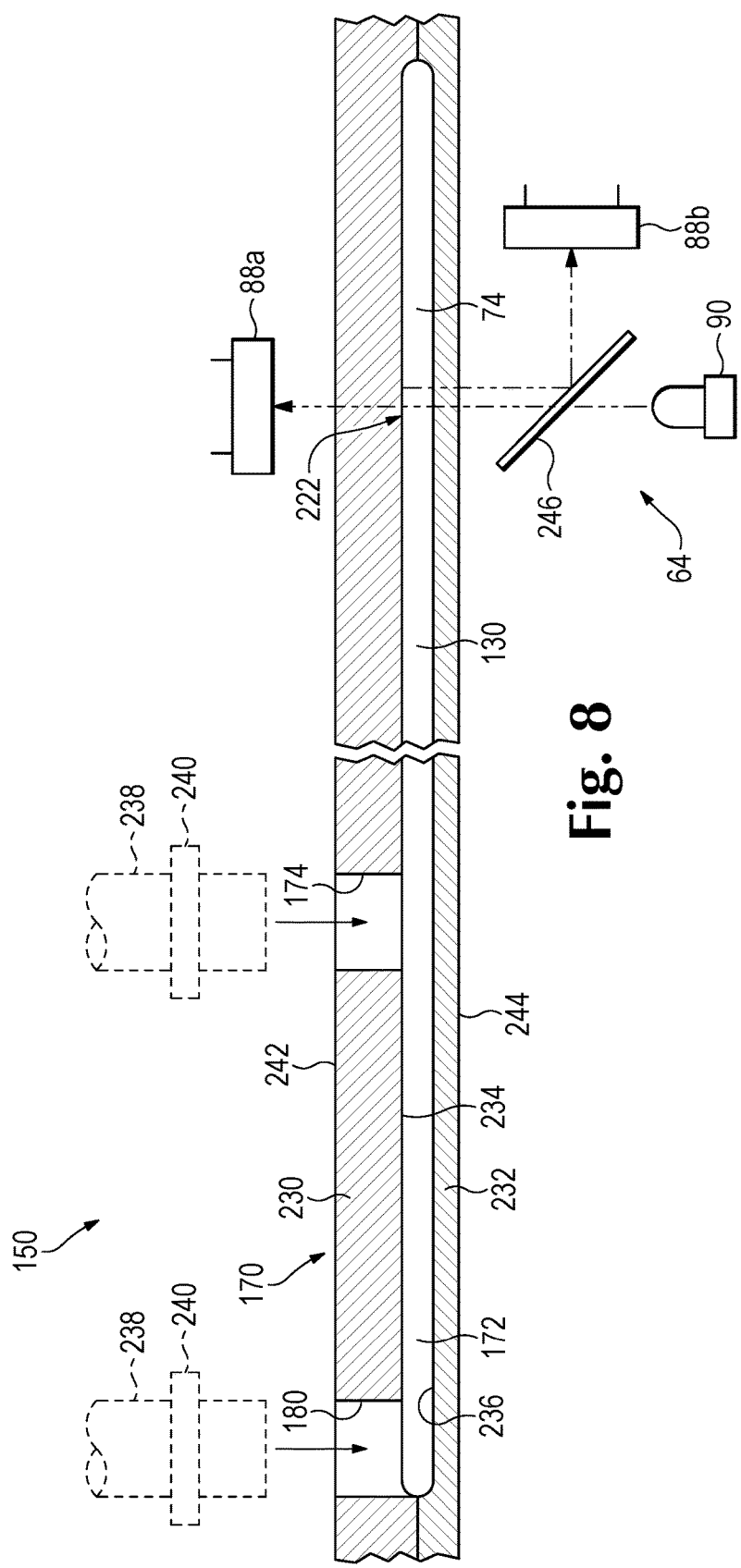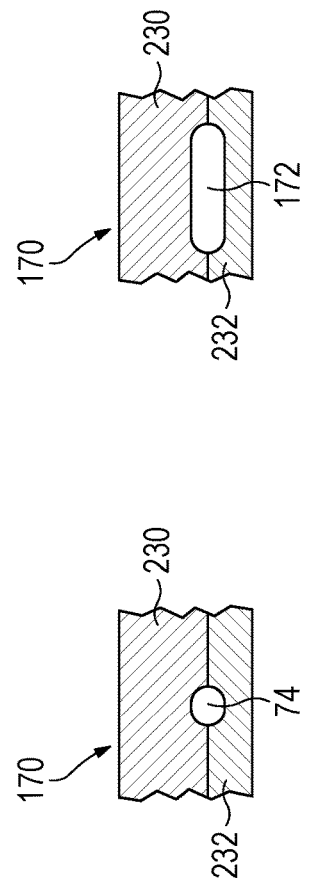

SYSTEM AND METHOD FOR DROPLET DETECTION

CROSS-REFERENCE TO PRIORITY APPLICATION

This application is based upon and claims the benefit under 35 U.S.C. § 119(e) of U.S. Provisional Patent Application Ser. No. 62/526,259, filed Jun. 28, 2017, which is incorporated herein by reference in its entirety for all purposes.

CROSS-REFERENCES TO OTHER MATERIALS

This application incorporates herein by reference in their entirety for all purposes the following patent documents: U.S. Patent Application Publication No. 2010/0173394 A1, published Jul. 8, 2010; U.S. Patent Application Publication No. 2011/0217712 A1, published Sep. 8, 2011; U.S. Patent Application Publication No. 2011/0311978 A1, published Dec. 22, 2011; U.S. Patent Application Publication No. 2012/0190033 A1, published Jul. 26, 2012; U.S. patent application Ser. No. 15/394,605, filed Dec. 29, 2016; and U.S. patent application Ser. No. 15/394,624, filed Dec. 29, 2016.

INTRODUCTION

A biological sample can be analyzed for the level of a nucleic acid target using an emulsion-based strategy. Before the sample is divided into droplets, it can be combined with reagents to support amplification of the target, such as by the polymerase chain reaction (PCR). An emulsion including sample-containing droplets then may be formed, with the target present in only a subset of the droplets. The emulsion may be heated, such as thermally cycled, to encourage amplification of the target in each droplet containing at least one copy of the target. A signal may be detected from the droplets to permit determination of which droplets contain amplified target. The level of the target may be calculated using the number of droplets that are positive (or that are negative) for the target, and a total number of droplets, in what is described as a digital assay.

Droplets of the emulsion can be processed in a macro-fluidic environment followed by a microfluidic environment. For example, the droplets can be thermocycled in a macro-fluidic environment (e.g., a sealed well) while the droplets are within a bulk phase form of the emulsion. Droplets of the emulsion then can be transferred from the bulk phase form to a microfluidic environment, for detection of a signal from the droplets passing one-by-one through a detection zone of a microfluidic channel. Transport-dependent detection systems have been described for transferring droplets from a bulk phase emulsion to a microfluidic environment, and for organizing the droplets for serial passage through a detection channel from which a signal is detected (e.g., see U.S. Patent Application Publication No. 2010/0173394 A1, and U.S. Patent Application Publication No. 2011/0311978 A1).

Droplet-based digital assays often rely on statistical analysis of a droplet population from an emulsion to obtain a result. Generally, the assay is more accurate when a greater number of droplets are used, and the droplets have a uniform size such that the probability of each droplet receiving a copy of a target is the same. Unavoidable variations in droplet size can reduce accuracy. To correct for these variations, the size of each droplet can be determined by measuring its travel time through the detection zone of a detection channel. For example, deflection of light by the droplet can produce a waveform in a deflection signal detected from the detection zone, with the width of the waveform corresponding to droplet size. However, the reliability of the deflection signal as an accurate reporter of droplet size can be dependent on a uniform flow rate of fluid/droplets through the detection channel, and a uniform spacing between droplets.

It is advantageous to transfer a high percentage of the droplets of an emulsion into a detection system, to maximize droplet usage, and to have the droplets pass rapidly through a detection channel of the system at a relatively constant rate and well-spaced from one another. However, various factors can decrease the efficiency of droplet transfer and emulsion throughput, and the uniformity of fluid flow and droplet spacing over time. These efficiency decreases can make droplet assays less accurate and reproducible, because data is collected from fewer droplets, the signal detected from individual droplets may be affected by variable droplet deformation, and individual corrections for variation in the size of droplets may be unreliable.

Improved droplet detection systems are needed. These improved systems may produce higher droplet utilization, a greater rate of emulsion throughput, more consistent flow rates and droplet spacing, and/or a less variable droplet shape in the detection channel, among others.

SUMMARY

The present disclosure describes systems and methods for detection of a signal from droplets of an emulsion. An exemplary system may comprise a fluid transporter having a tube with an open end for aspirating droplets, a singulator to arrange the droplets in single file and to space the single-file droplets from one another, and a detection channel in optical communication with a detector configured to detect a signal from droplets. In some embodiments, the singulator may have a channel junction at which a stream of droplets in single file is combined with a stream of spacing fluid, and a tapered spacing channel extending downstream from the channel junction toward the detection channel. In some embodiments, the fluid transporter may suck droplet-containing fluid and spacing fluid through the detection channel from respective sources. In some embodiments, droplets may be subjected to a disaggregation routine before they are passed through the detection channel.

BRIEF DESCRIPTION OF THE DRAWINGS

FIG. 8 is a fragmentary, cross-sectional view of the flow cell of FIG. 6, taken generally along line 8-8 of FIG. 6, in the presence of a light source and a pair of operatively associated detectors, in accordance with aspects of the present disclosure.

FIG. 9 is another fragmentary, cross-sectional view of the flow cell of FIG. 6, taken generally along line 9-9 of FIG. 6, in accordance with aspects of the present disclosure.

FIG. 10 is still another fragmentary, cross-sectional view of the flow cell of FIG. 6, taken generally along line 10-10 of FIG. 6, in accordance with aspects of the present disclosure.

DETAILED DESCRIPTION

Figure 1:
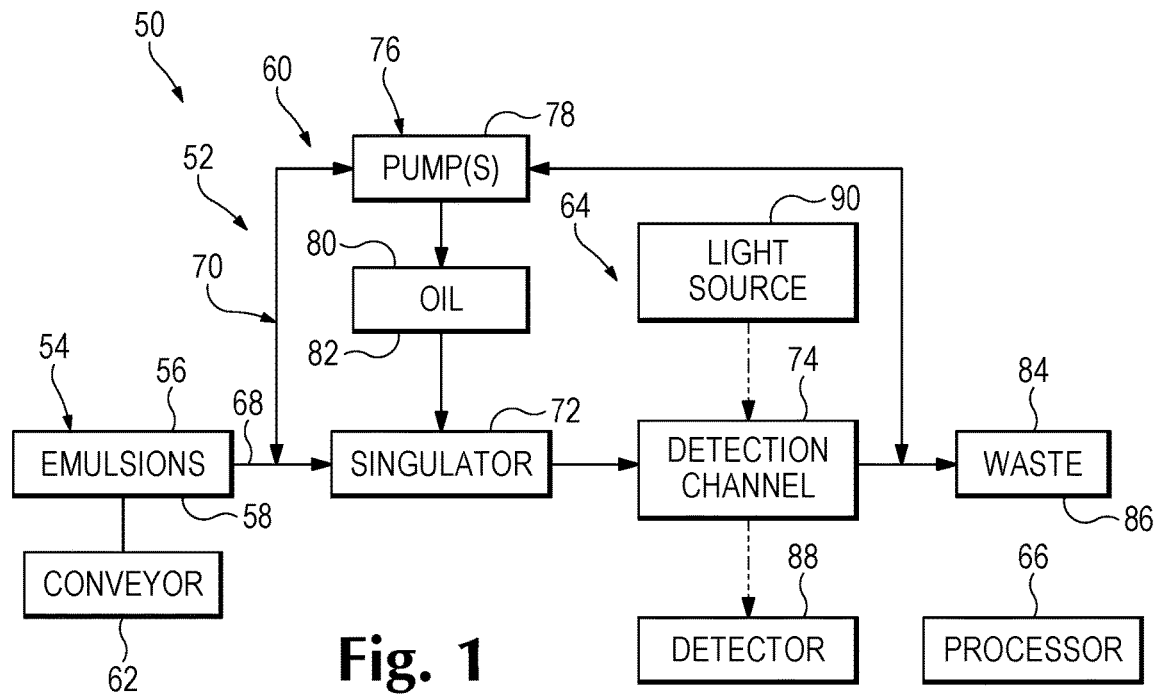
FIG. 1 is a schematic diagram of an exemplary system for droplet detection, in accordance with aspects of the present disclosure.

The present disclosure describes systems and methods for detection of a signal from droplets of an emulsion. An exemplary system may comprise a fluid transporter having a tube with an open end for aspirating droplets, a singulator to arrange the droplets in single file and to space the single-file droplets from one another, and a detection channel in optical communication with a detector configured to detect a signal from droplets. In some embodiments, the singulator may have a channel junction at which a stream of droplets in single file is combined with a stream of spacing fluid, and a tapered spacing channel extending downstream from the channel junction toward the detection channel. In some embodiments, the fluid transporter may suck droplet-containing fluid and spacing fluid through the detection channel from respective sources. In some embodiments, droplets may be subjected to a disaggregation routine before they are passed through the detection channel.

An exemplary method of droplet detection is described. In the method, a single-file stream of droplets in carrier liquid may be generated. At least one stream of spacing fluid may be combined with the single-file stream of droplets in carrier liquid. The combined streams may be directed to a detection channel using a spacing channel that tapers toward the detection channel. A distance between adjacent droplets may be increased as such droplets travel along the spacing channel toward the detection channel. A signal may be detected from droplets passing through the detection channel.

An exemplary detection system for droplets is described. The system may comprise a channel network including a sample inlet channel, at least one spacing-fluid inlet channel, and a spacing channel that meet one another at a channel junction, and a detection channel in communication with the channel junction via the spacing channel. The system also may comprise a spacing-fluid source connected to the channel network. The system further may comprise a detector in optical communication with the detection channel. One or more positive/negative pressure sources may be operatively connected to the channel network and configured to drive droplet-containing fluid from an emulsion source to the channel junction via the sample inlet channel, spacing fluid from the spacing-fluid source to the channel junction via the at least one spacing-fluid inlet channel, and droplet-containing fluid combined with spacing fluid from the channel junction and through the spacing channel and the detection channel. The sample inlet channel may taper toward the channel junction to force droplets into single file before such droplets reach the channel junction. The spacing channel may taper toward the detection channel to progressively increase a distance between adjacent droplets as the adjacent droplets travel from the channel junction to the detection channel.

The method and system of the preceding two paragraphs, and additional embodiments described elsewhere herein, such as in Section VI, may solve various problems including insufficient and/or inconsistent separation between detected droplets, an inadequate rate of droplet throughput, and/or droplet damage (fusion/fragmentation) as droplets are aligned and spaced, among others.

Another exemplary method of droplet detection is described. In the method, an open end of a tube and a well may be moved relative to one another to create contact between the open end and a sample held by the well. The sample may be an emulsion including droplets surrounded by carrier liquid. Suction may be applied downstream of a detection channel. The suction may draw (i) droplet-containing carrier liquid from the well and into the tube via the open end, and through a channel junction and the detection channel, and (ii) spacing fluid through the junction and the detection channel. A stream of the spacing fluid may be combined with a stream of the droplet-containing carrier liquid at the channel junction upstream of the detection channel. A signal may be detected from droplets passing through the detection channel.

Another exemplary system for droplet detection is described. The system may comprise a well to hold an emulsion including droplets surrounded by a carrier liquid. The system also may comprise a tube having an open end. The well and the open end may be movable relative to one another to create contact between the open end and the emulsion. The system further may comprise a channel junction, a detection channel, and a detector. The detector may be in optical communication with the detection channel and configured to detect a signal from droplets passing though the detection channel. A source of suction may be located downstream of the detection channel and configured to apply suction that drives (i) droplet-containing carrier liquid from the well and into the tube via the open end, and through the channel junction and the detection channel, and (ii) spacing fluid through the channel junction and the detection channel. A stream of the spacing fluid may be combined with a stream of the droplet-containing carrier liquid at the channel junction upstream of the detection channel.

The method and system of the preceding two paragraphs, and additional embodiments described elsewhere herein, such as in Section VI, may solve various problems including inadequate coordination between pumps, unpredictable and undesirably variable flow rates, and/or contamination due to droplets being trapped upstream of a detection channel, among others.

Yet another exemplary method of droplet detection is described. In the method, a tube and a well may be moved relative to one another to create contact between an open end of the tube and an emulsion held by the well. Fluid of the emulsion may be aspirated from the well via the open end of the tube. At least a portion of the aspirated fluid may be dispensed back into the well via the open end of the tube. Droplets of the emulsion may be transported from the well, via the open end of the tube, and to a detection channel, after the steps of aspirating and dispensing. A signal may be detected from droplets passing through the detection channel. The step of dispensing may disaggregate droplets of the emulsion. The method and additional embodiments described elsewhere herein, such as in Section VI, may solve various problems including inefficient transfer of droplets from a bulk phase emulsion to a microfluidic detection channel, and/or inadequate and/or variable separation between droplets in the detection channel, among others.

Further aspects of the present disclosure are described in the following sections: (I) detection system and method overview, (II) suck-through detection system and method, (III) singulator, (IV) suction loading, push-through detection system, (V) droplet disaggregation, and (VI) selected embodiments.

I. Detection System and Method Overview

This section provides an overview of exemplary systems and methods for droplet detection; see FIG. 1.

FIG. 1 schematically depicts selected components of an exemplary system 50 for droplet detection. The system includes a reader instrument 52 (interchangeably termed a droplet reader) to transport, arrange, separate, and detect droplets (also called reading droplets). An emulsion source 54, such as a sample holder 56 containing one or more emulsions 58, supplies droplet-containing fluid of the emulsions to instrument 52. Instrument 52 also may be configured to disaggregate droplets in some embodiments (see Section V). The reader instrument 52 may incorporate a fluid transporter 60, a conveyor 62 (interchangeably called a drive mechanism), a detection module 64, and a processor 66 (which may be called a controller) that are connected to, operatively associated with, and/or in communication with, one another.

Each emulsion 58 may include droplets surrounded, such as encapsulated, by a carrier fluid, which forms a continuous phase of the emulsion. The droplets may be substantially uniform in size (also called monodisperse), and/or may be aqueous. Each droplet may contain a label, such as a photoluminescent label. The carrier fluid may be liquid, and may comprise hydrophobic fluid, which may constitute the majority of the carrier fluid. The hydrophobic fluid may be oil. The droplets may have a density that is less or more than the density of the carrier fluid, such that the droplets are buoyant or sink in the carrier fluid.

Only a subset of the droplets may contain at least one copy of a target, such as a nucleic acid target. The target may have been amplified in a subset of the droplets prior to analysis with the detection system. A signal detected from the label may allow a determination, with processor 66, of which individual droplets contain the target. Target-positive or target-negative droplets may be enumerated. A level, such as a concentration, of the target may be calculated using the number of target-positive or target-negative droplets, and the total number of droplets (positive and negative). The total number of droplets in an emulsion and/or the number of droplets of the emulsion processed by the system (including signal detection) may be at least about $10^2$, $10^3$, $10^4$, $10^5$, or $10^6$, among others. Further aspects of droplet-based assays including droplets, emulsions, emulsion formation, targets, target amplification, signal detection, enumeration of positives/negatives, and calculation of target levels, among others, are described in the patent documents listed above under Cross-References, which are incorporated herein by reference.

Fluid transporter 60 may be any assembly configured to actively or passively take in droplet-containing fluid from emulsion source 54, hold fluid, drive fluid flow into, within, and/or between compartments of the assembly, and/or direct fluid flow. Exemplary directions of fluid flow are shown in FIG. 1 by solid linear arrows and solid angular arrows extending between labeled boxes; propagation of optical radiation is indicated with broken linear arrows. The fluid transporter may have a port 68 at which emulsion fluid enters (and optionally exits) the transporter, and a channel network 70 to direct fluid flow and including a singulator 72 and a detection channel 74. Transporter 60 also may have one or more valves to adjust fluid flow and/or change fluid flow paths within channel network 70, and one or more sources of positive/negative pressure 76 including one or more pumps 78, to drive fluid flow into, within, and/or out of transporter 60. The transporter further may include one or more reservoirs/receptacles, such as a reservoir 80 and any associated channel(s) to supply spacing fluid 82 (e.g., oil) to singulator 72, and a waste receptacle 84 to receive and store waste fluid 86. The same spacing fluid (also called transporter fluid) may be used for priming the transporter, droplet disaggregation, droplet spacing, rinsing, flushing, and/or the like, as described more fully below. The waste fluid may be droplet-containing fluid combined with spacing fluid that has passed through the detection channel, spacing fluid that has flushed portions of channel network 70 to prepare the transporter for reading droplets of another emulsion, and/or the like.

Port 68 may be formed by an open end of a tube. The open end may be located at a bottom end of the tube. In some embodiments, the tube may be a hollow needle. The tube may have any suitable size and shape. For example, the tube may have a uniform or varying inner diameter and outer diameter. The shape of the inside of the tube, and the shape of the outside of the tube, may or may not correspond to one another. The tube may be more rigid than tubing that connects the tube to other portions of the channel network, such as to a channel junction and/or a flow cell. In some embodiments, the use of flexible tubing between the tube and a flow cell prevents the jarring of the tube (e.g., if the tube pierces a sealing member to access a well) from being transmitted to the flow cell and associated optics of the detection module. The tube and tubing may be formed of the same or different materials. For example, the tube may be formed of metal (e.g., stainless steel), glass, or a hard polymer, and the tubing may be formed of polymer, among others. Exemplary flexible tubing may, for example, be fluoropolymer tubing, which may be PFA (perfluoroalkoxy), FEP (fluorinated ethylene propylene), PTFE (polytetrafluoroethylene), PVDF (polyvinylidene difluoride), or the like.

Channel network 70 includes a plurality of channels. A "channel," as used herein, is a compartment or passage, typically elongated, for conveying fluid and directing its flow. The channel may be bounded circumferentially by one or more walls at positions along its length to constrain the fluid radially. The channel may have any suitable cross-sectional shape, such as circular, oval, polygonal, or the like, with the shape being uniform or varying along the channel's length. Any of the channels of the channel network, and particularly the channels of singulator 72 and detection channel 74, may be a microfluidic channel, which means that the channel has a minimum or average cross-sectional dimension of less than one millimeter, such as less than 500, 400, 300, or 200 micrometers, among others. Each channel may be formed by a relatively rigid tube, relatively flexible tubing, a flow cell, or a combination thereof, among others. At least three channels of the channel network may intersect one another at a channel junction of singulator 72, as described in more detail below. The channel junction interchangeably may be described as a confluence region. In some embodiments, the at least three channels may be formed integrally with one another, such as by a flow cell. One or more pairs of channels of the channel network may be joined seamlessly, end-to-end, to create at least one longer channel, which may be composed of at least a pair of longitudinally aligned shorter channels. Each channel may be formed by tubing, a planar member (such as a flow cell), a connector, and/or the like.

Singulator 72 is any device or structure that is configured to arrange droplets in single file and/or increase a distance between droplets traveling within and/or through the device or structure. The distance may be measured between adjacent droplets from center to center, as an edge-to-edge spacing between the adjacent droplets, or the like. The process of arranging droplets in single file and/or increasing the distance between droplets is described as singulation and may separate droplets from one another, or increases the separation thereof, to improve detection of a signal from individual droplets substantially independently of each other. In some embodiments, the singulator may increase an average distance between droplets arranged in single file along at least a portion of a flow path.

Detection channel 74 of channel network 70 may be located downstream of singulator 72, and may convey droplets through a detection zone of the channel from which a signal is detected by detection module 64. The detection channel may or may not be formed integrally with the singulator. The detection channel, at the detection zone, may have a width and/or diameter that corresponds to the nominal diameter of droplets being read, where the nominal diameter is an average diameter defined by the droplets when spherical (i.e., undeformed). For example, the nominal diameter may be within about 50%, 25%, 20%, 15%, 10%, or 5% of the width/diameter of the channel. However, the droplets may be deformed substantially from a spherical shape in the detection channel by viscous forces as the droplets are driven through the channel.

Each source of positive/negative pressure 76 may be any device or mechanism configured to generate a pressure differential that drives fluid flow longitudinally in one or more channels. Source 76 may create suction (negative pressure) downstream of channels to draw fluid toward the source along a flow path, may create positive pressure upstream of channels to push fluid away from the source along a flow path, or both at respective different times. Exemplary sources that may be suitable include a pump 78, which may be driven with a motor. Exemplary pumps that may be suitable include positive displacement pumps, such as syringe pumps, peristaltic pumps, piston pumps, and diaphragm pumps, among others. The pump may or may not have an integrated valve.

Reservoir 80 holds spacing fluid 82 that is supplied to singulator 72 via one, two, or more channels of channel network 70. The spacing fluid may be a fluid that is miscible or immiscible with the carrier fluid (i.e., a continuous phase) of each emulsion. The spacing fluid and the carrier fluid may be a spacing liquid and a carrier liquid, respectively. The droplets of the emulsion may be hydrophilic, such as aqueous, and the spacing and carrier liquids each may be a hydrophobic liquid, such as a liquid comprising oil, with oil optionally constituting a majority of each fluid. The oil may be or include fluorinated oil (e.g., a perfluorinated oil), silicone oil, fluorosilicone oil, mineral oil, vegetable oil, or the like. The carrier liquid and/or the spacing liquid also may include a surfactant, which may stabilize the droplets. In some embodiments, the spacing fluid may be hydrophilic (e.g., aqueous) or gas, and the carrier fluid of the emulsion may be hydrophobic, or vice versa. The spacing fluid also may be called and/or function as a priming/filler fluid to fill some or all of the fluid lines of the transporter before an emulsion is loaded, and/or as a flushing fluid to flush droplets from channels located upstream of detection channel 74, when preparing instrument 52 to receive and detect droplets of a different emulsion.

The relative terms "upstream" and "downstream," as used herein, relate to fluid movement for a singulation/detection phase of system operation, unless specified otherwise. More specifically, fluid moves from an upstream region or element toward a downstream region or element during the singulation/detection phase or other specified phase of operation. The term "toward," as used herein for fluid movement with respect to an element or region, means along a fluid flow path that leads to the element or region. Generally, during the singulation/detection phase of system operation, fluid moves from upstream emulsion source 54 and upstream reservoir 80 to downstream singulator 72, and through the singulator to detection channel 74 further downstream.

Conveyor 62 is any device(s) or mechanism(s) that drives movement of port 68 of instrument 52 and emulsion source 54 (e.g., a well thereof) relative to one another, to create contact between the port and an emulsion of the source. The conveyor may drive motion of the emulsion source (and a sample holder/emulsion thereof) while the port remains fixed, motion of the port while the emulsion source remains fixed, or motion of both the emulsion source and the port. The motion may produce vertical displacement to change an elevation of the port and the source relative to one another (e.g., to create or break contact between the port and an emulsion, and/or to change the height of the port within the emulsion/well). The motion also or alternatively may produce horizontal displacement to align the port successively with different wells/emulsions. In some embodiments, the conveyor may be configured to drive movement independently along each of three orthogonal axes (e.g., x, y, and z), and/or may be configured to drive net relative movement in three-dimensional space. The conveyor may include at least one motor to drive motion, and, in some embodiments, may include at least two or three motors to drive net motion in three dimensions. At least one sensor may be incorporated to sense position/movement of the port and emulsion source relative to one another. Accordingly, in some embodiments, the conveyor may include at least one, two, or three servomotors, among others.

Detection module 64 may include at least one detector 88 configured to detect at least one signal from droplets passing through a detection zone of detection channel 74. The detector may detect electromagnetic radiation (e.g., optical radiation), an electrical or magnetic property, or subatomic particles (e.g., alpha or beta particles), among others. Detecting a signal may include detecting radiation, energy, a property, and/or particles, among others, and creating a signal (e.g., an electrical signal) corresponding to the radiation, energy, property, and/or particles detected. The detection zone may represent only a portion of the detection channel. The portion may be only part of the length of the detection channel. For example, the detection zone may have a longitudinal extent, measured along the flow path of the channel, that is less than the diameter of the droplets being detected.

Detector 88 may include an optical detector that is in optical communication with the detection zone and configured to detect optical radiation (i.e., ultraviolet, visible, and/or infrared light) therefrom. Optical communication may be created by one or more optical elements located in an optical path between the detection zone and the optical detector. The optical elements may direct light from the detection zone to a photosensitive receiving area of the detector. Exemplary optical elements that may be suitable include mirrors, lenses, beam splitters, fiber optics, slits, masks, filters, and the like. The optical elements may form a condenser and an objective.

The optical detector may include one or more photosensors to detect optical radiation. Each photosensor may, for example, convert light into electrical current or voltage. Exemplary photosensors include silicon photomultipliers, photodiodes, phototransistors, active-pixel sensors, charge-coupled devices, etc. In some embodiments, detector 88 may include a photoluminescence detector to detect light emitted from droplets, and/or a deflection detector to detect light deflected by the droplets by refraction, reflection, Mie scattering, and/or the like. Further aspects of detectors and their use in droplet detection systems are described in the patent documents listed above under Cross-References, particularly U.S. patent application Ser. No. 15/394,605, and U.S. patent application Ser. No. 15/394,624, which are incorporated herein by reference.

For optical detection, detection module 64 may include at least one light source 90 to irradiate the detection zone with optical radiation. The light source may generate excitation light to induce photoluminescence from the droplets, and particularly a photoluminescent label thereof. Alternatively, or in addition, the light source may generate incident radiation that is detected after passing through the detection zone. Exemplary light sources that may be suitable include solid-state light sources (e.g., light-emitting diodes), lasers, high-intensity discharge lamps, etc.

Processor 66 includes one or more electronic circuits, which may be integrated circuits, to control and coordinate operation of other components of system 50 and/or to process data received from the components. Exemplary processors may include a central processing unit, a peripheral processing unit, a field-programmable gate array, and/or the like. The processor may be configured to control/operate other components of the system utilizing instructions, which may be encoded by software or hardware, among others. The instructions may, for example, be carried by the processor or provided by an external storage source, such as memory. The processor may be in communication with fluid transporter 60, such as an actuator/controller of each positive/negative pressure source 76 and/or valve of the transporter. Signals from the processor may determine when each source 76 is active, whether the source is generating positive or negative pressure, and a fluid flow rate produced by the source. The processor also may send signals that close, open, switch, or otherwise adjust each valve as appropriate. Processor 66 also may operate conveyor 62 to change the positional relationship of emulsion source 54 and port 68, as described in more detail elsewhere herein, such as in Sections II and V, among others. The processor further may be in communication with detection module 64, to, for example, send activating signals to the detector and receive detected signals therefrom.

II. Suck-Through Detection System and Method

This section describes exemplary embodiments of the systems and methods of Section I, in which suction is applied downstream of detection channel 74; see FIGS. 2-5. The systems and methods of this section may be combined with, or modified by, any suitable aspects and features of the systems and methods disclosed in other sections, including Sections I, III, IV, V, and VI.

The detection system of Section IV divides the processing of an emulsion into sequential phases. During a loading phase, droplets of the emulsion are loaded into a fluid transporter. For example, the fluid transporter may pick up droplets of an emulsion by sucking them through a long tube and a valve, and into a holding coil. After droplet loading has been completed, the system switches to a singulation/detection phase by adjusting the valve, and then all of the loaded droplets pass through a singulator and a detection channel.

In contrast, the detection systems of this section can suck droplets continuously from a bulk phase emulsion into a fluid transporter, and through a singulator and detection channel thereof. This "suck-through" design can greatly simplify the fluid-carrying portion of the fluid transporter located upstream of the detection channel. For example, the suck-through design, relative to the embodiment of the system of Section IV, may relocate tubing, fittings, and a valve within the fluid transporter from upstream to downstream of the detection channel. All of these components are potential sites where droplets can get trapped. By operatively locating these components past the detection channel, the potential for droplet carryover is greatly reduced, and droplet reading performance is improved.

The suck-through design may be enabled by channel size/geometry and the configuration of the conveyor. First, the length of the detection channel may be reduced to a minimum length sufficient for allowing droplets to stabilize in shape after they have been spaced from each other upstream of the detection channel. Since the detection channel may determine the minimum diameter of the flow path that droplets follow in the transporter, shortening the detection channel can substantially reduce the overall flow resistance, and thus the size of the pressure drop within the transporter. A smaller pressure drop means less gas bubble formation within the transporter, resulting in more consistent and predictable flow. Also, droplets may cluster less as they pass through a shorter detection channel, such that a higher percentage of the droplets are sufficiently resolved from one another in the detected signal. Second, a pickup tube of the fluid transporter that contacts emulsions held by a sample holder (e.g., a multi-well plate) may be fixed in position, and the sample holder may be moved with respect to the pickup tube to create contact between the tube and each emulsion. This arrangement allows the system's singulator and detection module (including the detection channel and optics) to be rigidly mounted relative to one another. Rigidly mounted optics may be advantageous: the optics can be bulky and difficult to move rapidly, and the risk of disturbing the alignment of optical components is avoided.

Minimizing the pressure drop along the detection channel can be very important to the successful implementation of a suck-through design. The pressure at the outlet end of the detection channel may be equal to atmospheric pressure (the pressure at the open end of the pickup tube) minus the pressure drop. Without minimizing the pressure drop, the low pressure at the outlet of the detection channel may be close to or below the vapor pressure of the transporter/emulsion fluid, which can bring it to boiling, or at least close to boiling. The low pressure also can cause dissolved gases in the transporter/emulsion fluid to come out of solution. When vapor appears in the channel network of a fluid transporter, the transporter can lose hydraulic stiffness, which can cause flow velocity fluctuations to increase dramatically. These fluctuations can make detection of droplet size more challenging, and increase signal amplitude variation.

When droplets of different diameter travel along the same capillary, larger droplets travel more slowly. If the channel length between the channel junction of the singulator and the detection channel is great enough, larger droplets may be followed closely by one or more smaller ones that have caught up with the larger droplets. Since the portion of the detected signal that is attributable to an individual droplet may be more accurate if the droplets have at least a minimum separation, droplets that are too close to one another may be rejected. Accordingly, a decreased distance between the singulator and the detection channel, relative to the prior art, may allow a suck-through design to reject fewer droplets due to lack of separation.

The suck-through design is also an improvement because it can use a single pump to draw droplet-containing fluid of an emulsion and spacing fluid through a singulator and detection channel. In contrast, another system relies on two pumps to push the respective fluids through the singulator and detection channel (e.g., see Section IV). These two pumps must be synchronized and function cooperatively to achieve proper droplet singulation and uniform flow rates. Accordingly, the suck-through design can provide a more consistent ratio of droplet-containing fluid and spacing fluid to the singulator.

Figure 2:
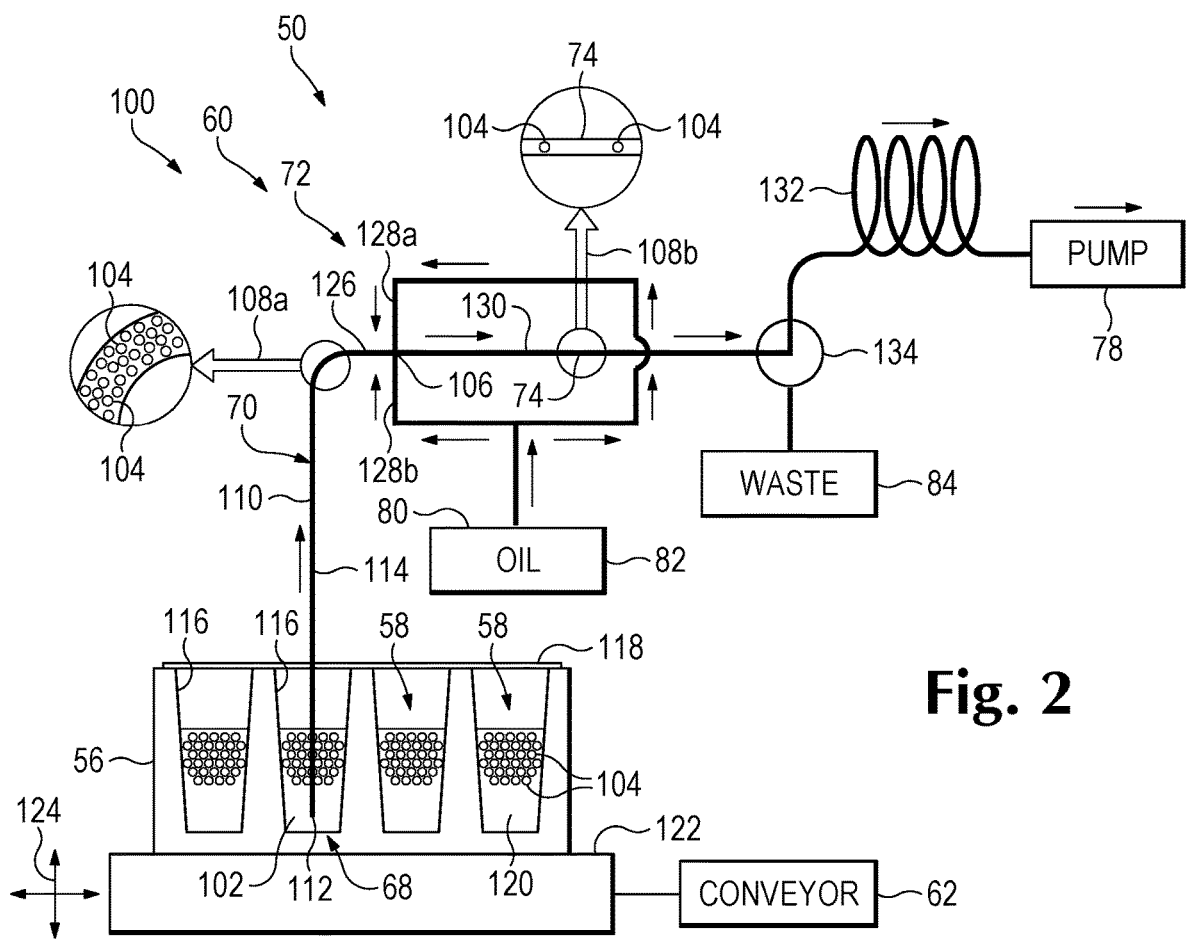
FIG. 2 is a schematic diagram of a fluid transporter and sample holder of an exemplary version of the system of FIG. 1 that uses suction to draw droplet-containing fluid of an emulsion and spacing fluid through an upstream channel junction and a downstream detection channel of the system, in accordance with aspects of the present disclosure.

FIG. 2 schematically illustrates a fluid transporter 60 and sample holder 56 of an exemplary version 100 of system 50. Detection system 100 may have any suitable combination of the components and features described above for detection system 50. System 100 has a "suck-through" design utilizing suction generated by one or more pumps, such as a single pump 78, to draw fluid 102 containing droplets 104 of each emulsion 58, and spacing fluid 82, through a singulator 72 including a channel junction 106, and through a detection channel 74 located downstream of the singulator. Pump 78 applies suction (negative pressure) to a channel network 70 at a position downstream of detection channel 74. Solid linear arrows located adjacent regions of the channel network indicate directions of fluid flow. Open arrows 108$a$, 108$b$ each extend from a respective section of the channel network encircled with a smaller circle, to a larger circle enclosing a magnified illustration of the encircled section.

Fluid transporter 60 defines an inflow path 110 for droplet-containing fluid 102 of emulsion 58. Inflow path 110 extends from port 68 to channel junction 106. Port 68 may be formed by an open end 112 of a tube 114, which may be a bottom end thereof. Accordingly, tube 114 defines at least an entry portion of inflow path 110.

Emulsions 58 may be held by respective wells 116 of sample holder 56. The wells may be arranged in a linear array or a two-dimensional array, among others. Each well may have a sealing member 118, such as a heat-sealable foil, attached to a top thereof, to seal the well. (In the depicted embodiment, the sealing member covers and seals all of the wells of the sample holder.) The sealing member may prevent evaporation (e.g., if the emulsion is thermally cycled to encourage target amplification before detection) and/or contamination.

Each emulsion 58 includes an immiscible carrier liquid 120 surrounding droplets 104. Suction applied by pump 78 draws droplet-containing fluid 102 (i.e., at least a portion of emulsion 58 including carrier liquid 120 and droplets 104) into channel network 70 via open end 112 of tube 114.

The droplets may form a buoyant pack overlying a substantially droplet-free region of the emulsion. In other embodiments, the droplets may sink to the bottom of the well to form a sunken pack, or may have neutral buoyancy such that they neither sink nor float. Methods to disperse droplets of a pack are described in Section V.

Open end 112 of tube 114 may be positioned in each well 116, and in contact with emulsion 58 therein, by operation of conveyor 62. In the depicted embodiment, sample holder 56 rests on a support 122 that is connected to conveyor 62 via a linkage. Operation of the conveyor moves the support, and thus sample holder 56, indicated by horizontal and vertical motion arrows at 124. Horizontal motion can align the open end of tube 114 serially with each of wells 116. Vertical motion can position the open end at a suitable height (interchangeably called an elevation) above the bottom of the well, such as near the bottom of the well as shown. In some embodiments, the vertical motion can pierce sealing member 118 to provide access to the interior of the well for tube 114.

Fluid transporter 60 aligns and spaces droplets 104. Droplets traveling along a wider portion of inflow path 110, magnified at 108$a$, at a position upstream of singulator 72, may be close to one another and randomly arranged in two or three dimensions (i.e., both across and along the flow path). However, in detection channel 74, magnified at 108b, droplets 104 are aligned with one another on the flow axis through the detection channel and have a substantially increased separation from one another parallel to the flow axis. The geometry of channel junction 106, and channels that meet one another at the junction, facilitate droplet alignment and separation. The channels may include a sample inlet channel 126, one or more spacing-fluid inlet channels 128a, 128b, and an intermediate channel such as a spacing channel 130, as described in more detail below. The intermediate channel may extend from channel junction 106 to detection channel 74, and/or may define at least a portion of a flow path extending from the channel junction to the detection channel.

Fluid that passes through detection channel 74 may be drawn into and collected in a holding region 132 (e.g., a holding coil) located at a position along a flow path from the detection channel to pump 78. The fluid may be pushed from the holding region to waste receptacle 84 with pump 78 after adjustment of a valve 134, which isolates the detection channel from the holding region and creates fluid communication between the holding region and the waste receptacle.

Figure 3:
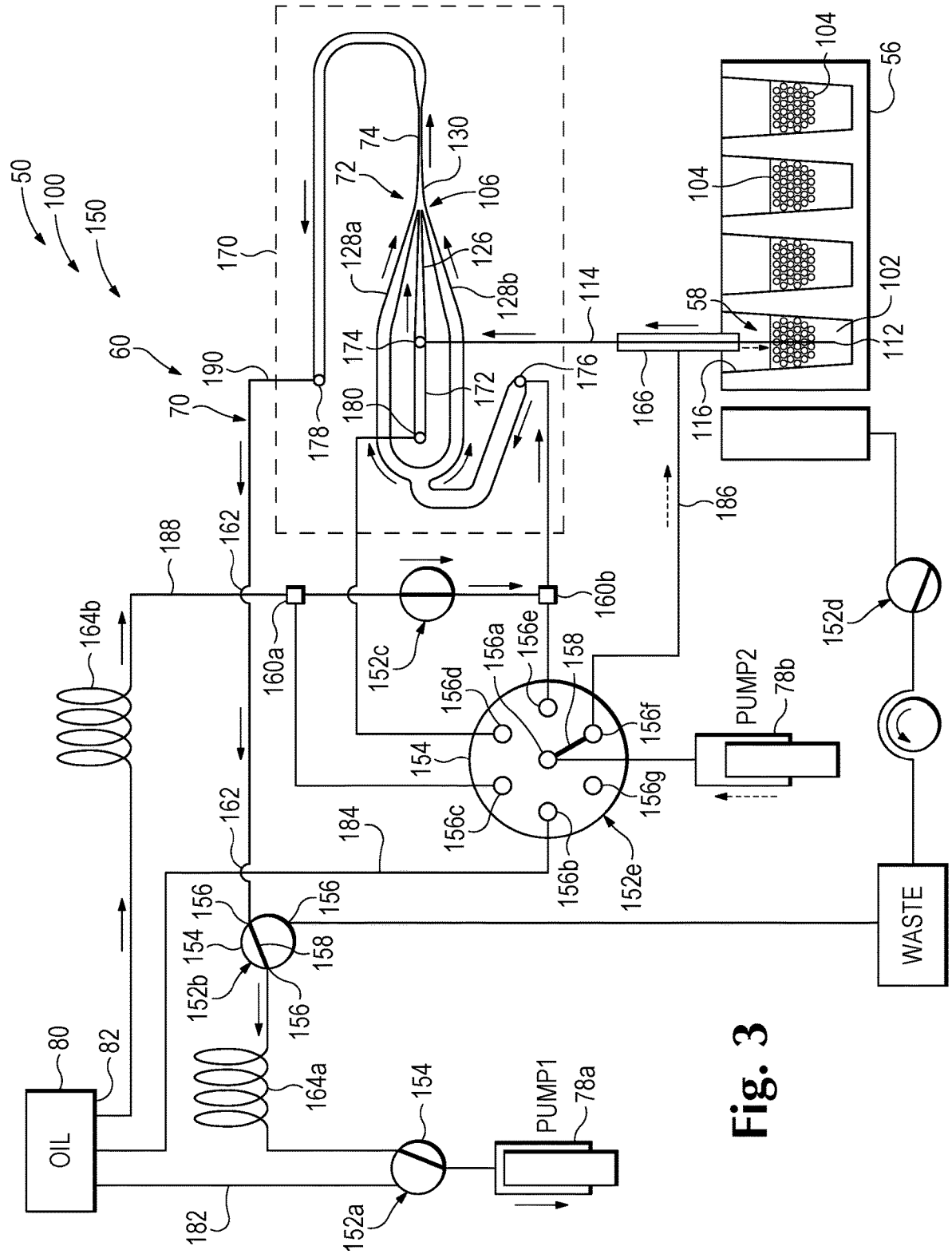
FIG. 3 is a schematic view of a fluid transporter and sample holder of an embodiment of the system of FIG. 2 that includes a singulating flow cell, taken during a detection phase of system operation while suction is being applied, with linear arrows indicating directions of fluid flow, in accordance with aspects of the present disclosure.

FIG. 3 shows a fluid transporter 60 and a sample holder 56 of an exemplary detection system 150 having a suck-through design, as generally shown in FIG. 2. System 150 may have any suitable combination of the components and features described above for systems 50 and 100. For example, system 150 may include a fluid transporter 60, a detection module, a processor, and/or a conveyor, among others, as described above for systems 50 and 100. Fluid flow into and within the transporter, for a detection phase (FIG. 3) or two exemplary procedures of a flushing phase (FIGS. 4 and 5), is indicated with linear arrows.

Pumps 78a, 78b, also called pump1 and pump2, respectively, drive fluid flow into and within fluid transporter 60, particularly a channel network 70 thereof. Each pump is configured to be operated selectably as a suction pump that applies negative pressure to draw fluid toward the pump, or as a discharge pump (a positive pressure pump) to push fluid away from the pump.

The pumps drive fluid flow within channel network 70 along various flow paths. The flow paths may be selected and/or modified by changing the position of one or more valves 152a-152e. Each valve has a body 154, represented by a circle, and two or more ports 156 (see valve 152b), such as ports 156a-156g (see valve 152e). At least one pair of ports of each valve may be placed in fluid communication with one another via a movable port connector 158 (see valves 152b and 152e). In the depicted embodiment, connector 158 is rotatable to create or break fluid communication between selected ports of the valve. Valves 152a and 152b may be three-port valves that are adjustable to select whether a first port communicates with a second port or a third port. Valves 152c and 152d may be two-port valves that are adjustable to connect or isolate a first port and a second port relative to one another. Valve 152e may be a multi-position valve in which connector 158 is rotatably adjustable to connect a central port 156a with any one of a plurality of different lateral ports 156b-156g.

Other features of channel network are also shown in schematic form. T-connectors 160a, 160b form respective junctions at which three channels communicate with one another. Sites at which lines representing separate channels cross one another include a semi-circular bump 162 in one of the lines to indicate that the channels are isolated from one another where they cross. Holding regions 164a, 164b of the channel network, which are configured to hold a greater volume of fluid, are shown as coils, and may be created by a long section of channel and/or a larger inner diameter of the channel. A sleeve 166 surrounds a portion of tube 114, optionally arranged coaxially therewith, and has an open bottom end. The sleeve and tube collectively may be described as a tip of the fluid transporter, which may be a coaxial tip. Further aspects of coaxial tips and their use in droplet detection systems are described in U.S. Patent Application Publication No. 2012/0190033 A1, which is incorporated herein by reference.

The system may include a flow cell 170 forming at least a portion of channel network 70 of fluid transporter 60. (The border of the flow cell is dashed to distinguish it from channels.) The term "flow cell," as used herein, is any member defining a fixed arrangement of channels, such as a network of interconnected channels, which may include at least three channels that meet one another. The channels of the flow cell may be formed integrally with one another, and/or the flow cell may have no moving parts. The flow cell may form a singulator 72 including a channel junction 106 at which a sample inlet channel 126, one or more spacing-fluid inlet channels 128a, 128b, and a spacing channel 130 meet one another. The flow cell also may form a detection channel 74 and a flushing channel 172. Exemplary relative sizes and geometries for the channel junction and channels are shown. In contrast, channels of channel network 70 outside of the flow cell are not drawn to scale, but instead are represented schematically with single lines. The flow cell may define a minimum width/diameter of the channel network and/or of a flow path from open end 112 to the detection channel; each channel outside the flow cell may be larger in width/diameter than the minimum width/diameter of one or more channels of the flow cell.

Flow cell 170 may define a plurality of ports at which fluid can enter and exit the flow cell. Exemplary ports include a sample port 174 for entry of a sample (i.e., droplet-containing fluid 102 of an emulsion 58) received from a well 116 of sample holder 56, a spacing-fluid port 176 for entry of spacing fluid 82 received from reservoir 80, an outflow port 178 for exit of fluid from the flow cell after passing through detection channel 74. Flow cell 170 also may define a flushing port 180 to facilitate flushing regions of the flow cell with spacing fluid 82 or another fluid, to remove trapped/residual droplets from at least part of the channel network, before droplet-containing fluid of another emulsion 58 is introduced into flow cell 170.

Transporter 60 may be prepared for use by filling channels of channel network 70 with spacing fluid 82 from reservoir 80, and drawing spacing fluid into one or both pumps 78a, 78b. Spacing fluid 82 may be drawn into pump 78a after adjusting valve 152a to create fluid communication between reservoir 80 and the pump along a priming/filling flow path 182. The spacing fluid also may be drawn into pump 78b after adjusting valve 152e, to align connector 158 with central port 156a and lateral port 156b, which creates fluid communication between reservoir 80 and the pump along a priming/filling flow path 184. The pumps then may drive spacing fluid 82 into other channels of the channel network, by suction and/or positive pressure after suitable adjustment of valves 152a-152e, as needed.

FIG. 3 shows system 150 in a detection phase of operation, as in FIG. 2 for system 100, with the bottom end of tube 114 in contact with one of emulsions 58. In the detection phase, pump 78a corresponds to pump 78 of system 100 and applies suction. In contrast, pump 78*b* may apply positive pressure to push a small amount of spacing fluid 82 into sleeve 166 via a rinsing flow path 186, to rinse the outside of a protruding, bottom end region of tube 114 as fluid of the emulsion is being aspirated from the well and into the tube. (Fluid flow along rinsing flow path 186 is indicated with dashed linear arrows.) Pump 78*b* thus may function, in part, to increase the percentage of droplets from a given well 116 that enters tube 114. Further aspects of a coaxial tip and its use are described in U.S. Patent Application Publication No. 2012/0190033 A1, which is incorporated herein by reference.

Pump 78*a* may apply suction downstream of detection channel 74, such as downstream of flow cell 170 and particularly outflow port 178 thereof. The suction creates a pressure differential between the pump and open end 112 of tube 114 sufficient to drive droplet-containing fluid 102 of emulsion 58 into and through tube 114 to sample port 174, and through the sample port, sample inlet channel 126, and channel junction 106.

At the same time, the suction also creates a pressure differential between pump 78*a* and reservoir 80. The pressure differential is sufficient to drive flow of spacing fluid 82 along a spacing flow path 188 between reservoir 80 and flow cell 170. Spacing flow path 188 extends from reservoir 80, through holding region 164*b*, valve 152*c*, and T-junction 160*b*, and to spacing-fluid port 176. The suction further drives the spacing fluid from spacing-fluid port 176, through spacing-fluid inlet channels 128*a*, 128*b*, and through channel junction 106, where at least one stream of the spacing fluid is combined with a stream of droplet-containing fluid of the emulsion. The suction further drives the combined streams of fluid through spacing channel 130 and detection channel 74 to outflow port 178, and out of the flow cell to holding region 164*a*. Suction may be applied until any suitable percentage of a given emulsion 58 and/or droplets thereof has passed through detection channel 74.

Any suitable pressure differential may be created between pump 78*a* and reservoir 80 and/or between the pump and open end 112 of tube 114. Either or both pressure differentials may be less than about 3, 2, or 1 pounds per square inch (psi) (i.e., less than about 20.7, 13.8, or 6.9 kilopascal (kPa)). The pressure differential between pump 78*a* and reservoir 80 may be adjusted by changing the diameter/length of tubing along flow path 188, and/or changing the elevation of reservoir 80 (and/or the fluid therein) and the pump relative to one another, among others. The pressure differential between pump 78*a* and open end 112 may be adjusted by changing the diameter/length of tubing along a flow path 190 extending from open end 112 to pump 78*a*, and/or changing the elevation of the pump and open end 112 relative to one another.

Figure 4:
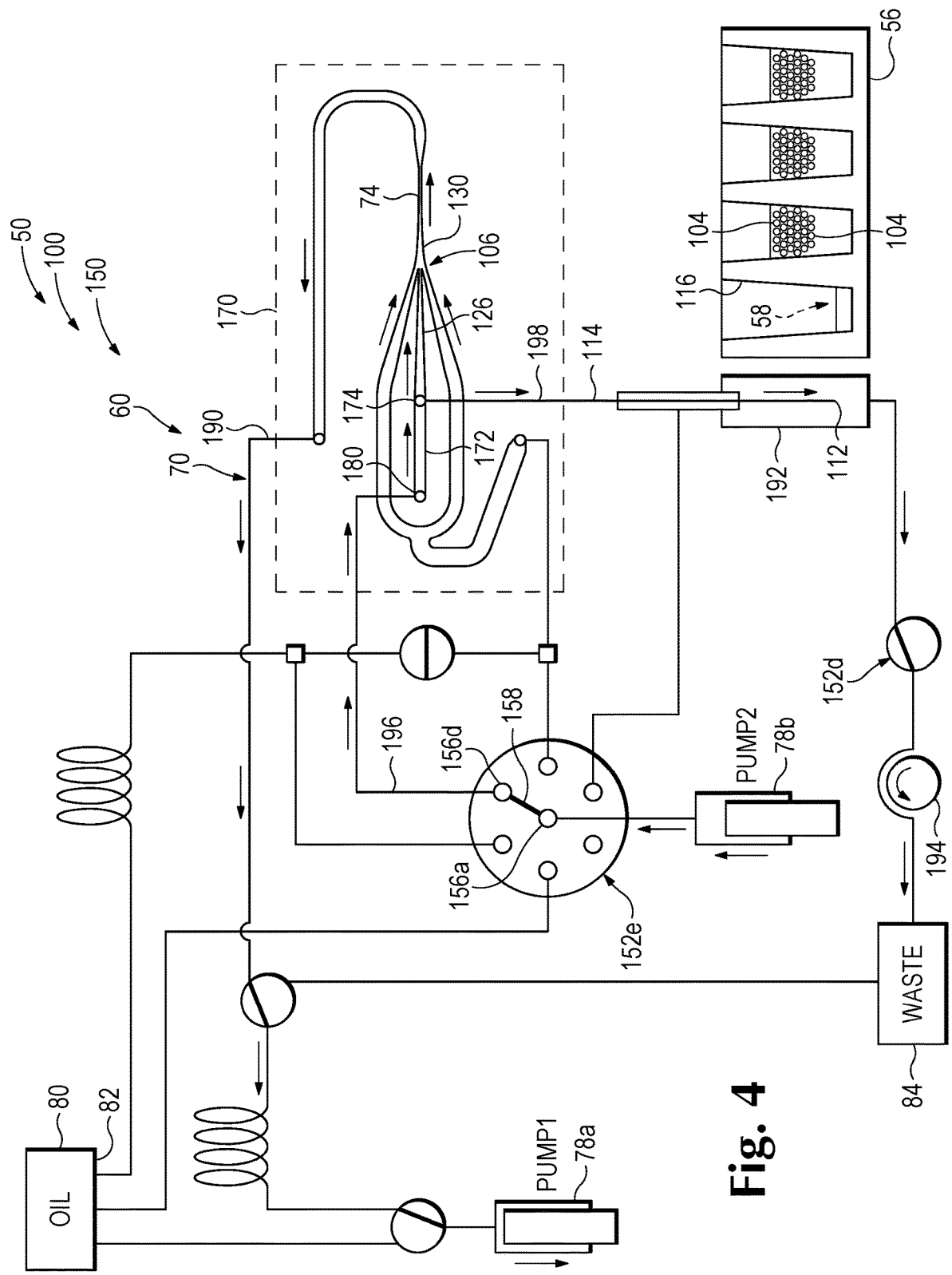
FIG. 4 is another schematic view of the fluid transporter and sample holder of FIG. 3, taken during a flushing phase following the detection phase (and before initiating another detection phase with a different emulsion), to remove residual droplets located in or upstream of the detection channel at the end of the detection phase, in accordance with aspects of the present disclosure.

FIG. 4 shows a configuration of fluid transporter 60 and sample holder 56 of system 150 during a flushing phase following the detection phase of FIG. 3. The flushing phase may remove residual droplets 104 of emulsion 58 located in channel network 70, such as at positions in or upstream of detection channel 74, to prepare the detection system for processing another emulsion. (Droplets lurking downstream of the detection channel following the detection phase generally do not pose a problem as contaminants, if fluid is never driven in reverse through the detection channel.) Before the flushing procedure is started, the bottom end of tube 114 may be removed from a well 116 of sample holder 56 and placed into alignment with and/or into a waste inlet 192, to avoid introducing any more droplets of emulsion 58 into the channel network. If needed, the waste inlet also may be placed in fluid communication with waste receptacle 84 by adjusting valve 152*d*. A pump, such as a peristaltic pump 194, may be operated to drive flow of waste fluid from waste inlet 192, through valve 152*d*, to waste receptacle 84.

Both pumps 78*a* and 78*b* are operating generally as in FIG. 3. Pump 78*a* applies suction to create a pressure differential between the pump and channel junction 106, using a portion of flow path 190 (similar to FIG. 3). Pump 78*b* pushes spacing fluid 82, which now functions as a flushing fluid, into flow cell 170 via a flow path 196 opened by adjusting valve 152*e* to create fluid communication between ports 156*a* and 156*d*. The spacing fluid enters the flow cell at flushing port 180 and flows to sample port 174 via flushing channel 172. A portion of the spacing fluid may be urged through channel junction 106, spacing channel 130, and detection channel 74 due to the suction applied by pump 78*a*, to flush residual droplets from sample inlet channel 126, spacing channel 130, and detection channel 74. Another portion of the spacing fluid may flow out of flow cell 170 via sample port 174, and toward open end 112 of tube 114, to flush droplets from a flow path 198 extending from sample port 174 to open end 112.

Figure 5:
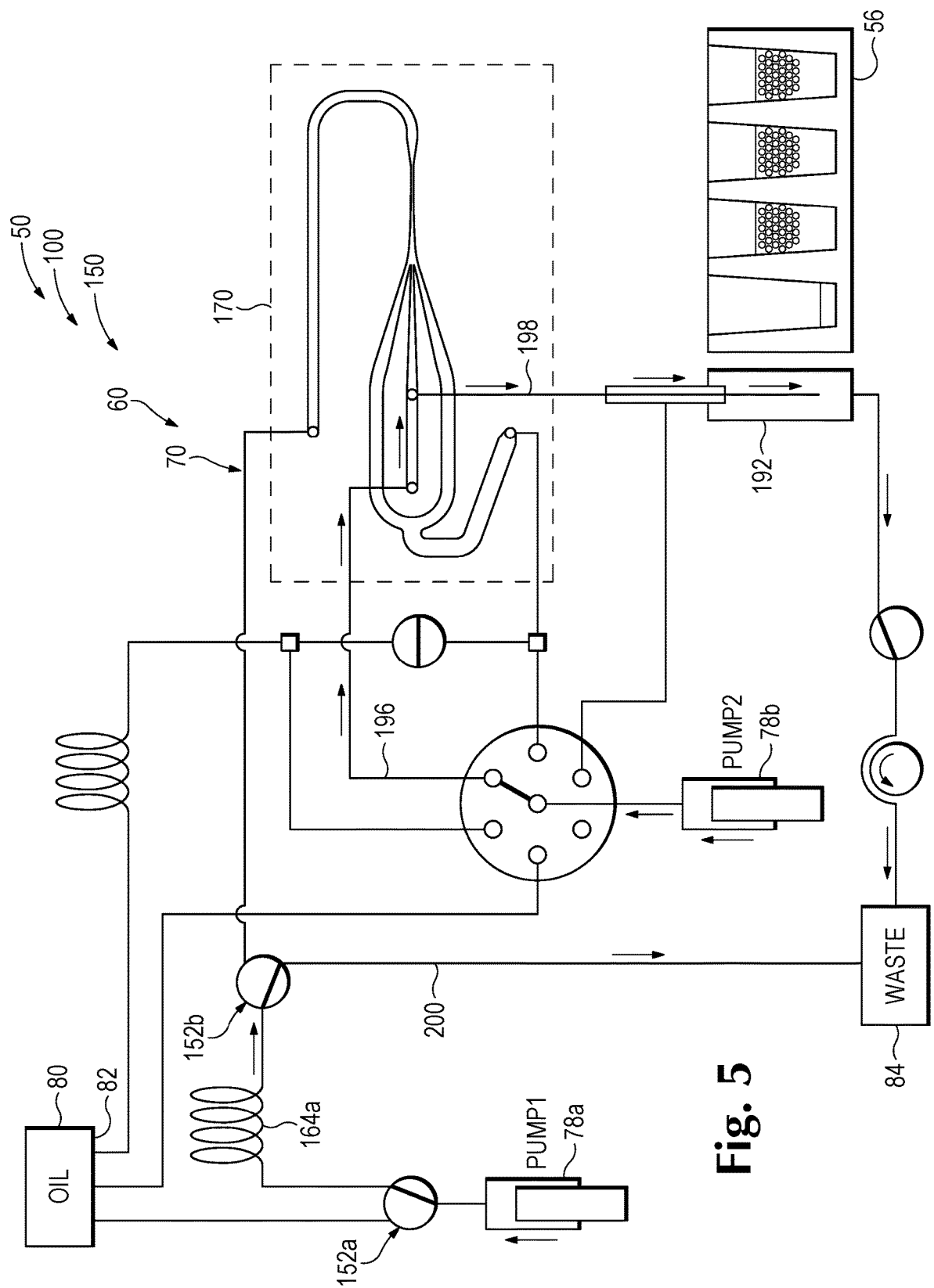
FIG. 5 is another schematic view of the fluid transporter and sample holder of FIG. 3, taken during the flushing phase and illustrating fluid flow to flush droplets from a droplet inflow line and to push previously detected droplets to waste, in accordance with aspects of the present disclosure.

FIG. 5 shows another configuration of fluid transporter 60 and sample holder 56 of system 150 during a flushing phase following the detection phase of FIG. 3. Both pumps 78*a* and 78*b* are active and pushing spacing fluid 82 into channel network 70. Valves 152*a*, 152*b* have been adjusted to open a flow path 200 between pump 78*a* and waste receptacle 84. Pump 78*a* is pushing fluid collected in holding region 164*a* to the waste receptacle. The collected fluid may include droplet-containing fluid of the emulsion and spacing fluid received from detection channel 74. Pump 78*b* is pushing spacing fluid, which functions as a flushing fluid, to waste inlet 192 via flow path 196, flow cell 170, and flow path 198, as in FIG. 4.

III. Singulator

This section describes further aspects of singulator configurations for any of the detection systems and methods of the present disclosure, as exemplified by flow cell 170; see FIGS. 6-10 (also see FIGS. 1-5).

Figure 6:
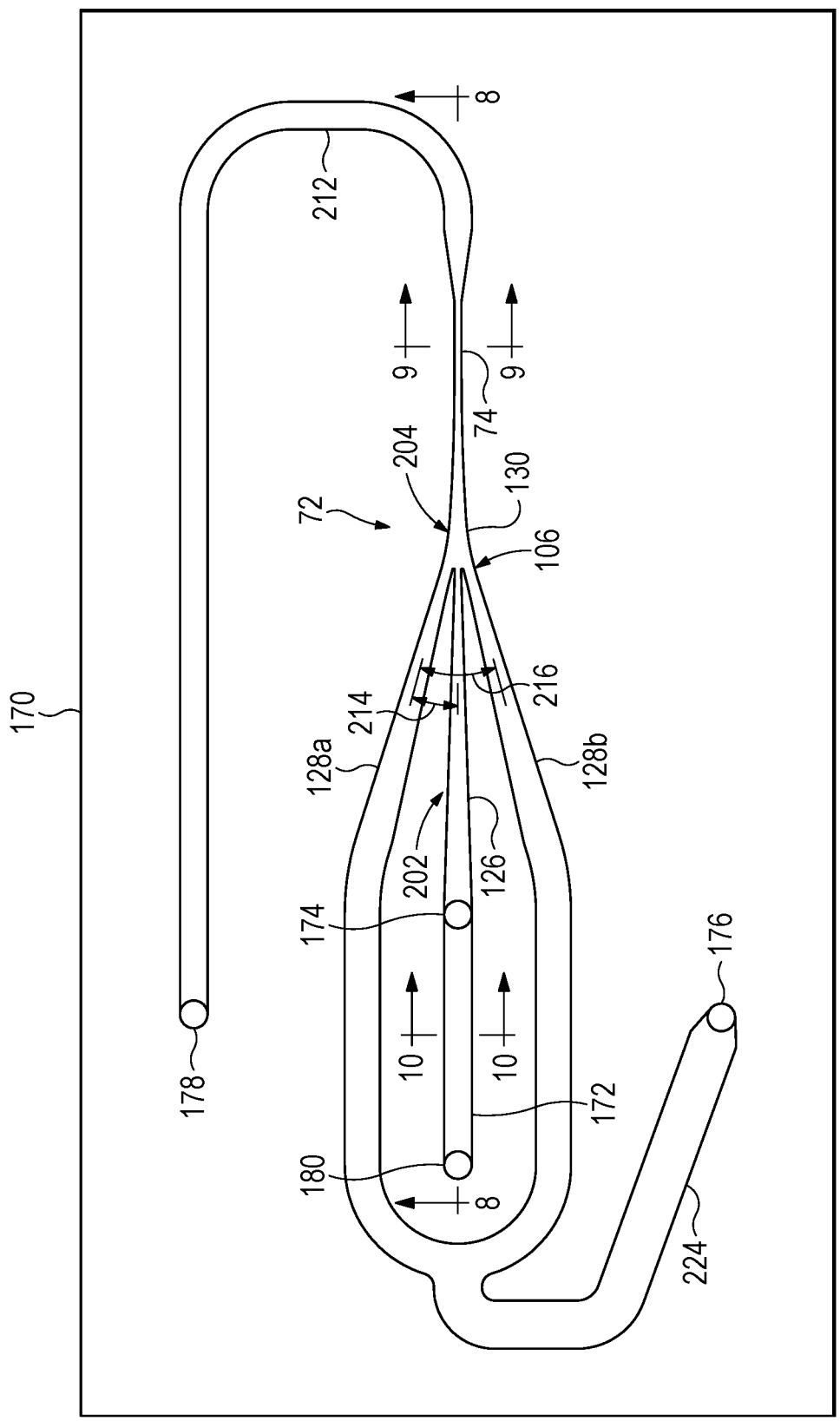
FIG. 6 is a plan view of the singulating flow cell of the fluid transporter of FIG. 3, taken in isolation from other system components, in accordance with aspects of the present disclosure.
Figure 7:
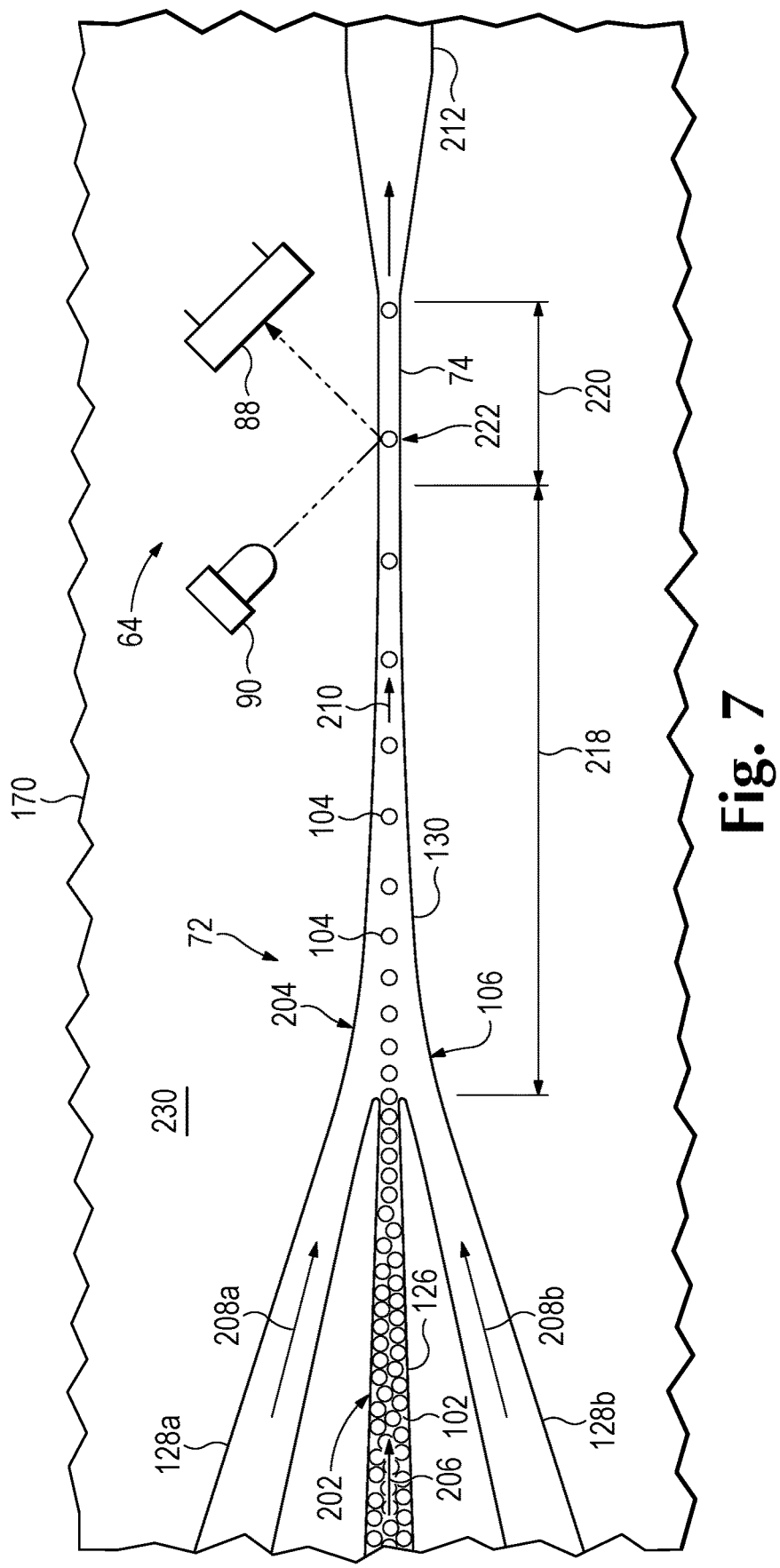
FIG. 7 is a fragmentary plan view of the flow cell of FIG. 6, taken around a channel junction and downstream detection channel during a detection phase of system operation while droplets are being arranged in single file upstream of the channel junction, and spaced from one another downstream of the channel junction before reaching the detection channel, with a light source and an operatively-associated detector of the system's detection module depicted schematically to identify a detection zone of the detection channel where droplets are detected, in accordance with aspects of the present disclosure.

FIG. 6 shows flow cell 170 of detection system 150 (also see Section II) in isolation from other system components; and FIG. 7 shows a fragmentary portion of the flow cell arranging droplets 104 during a detection phase of system 150 operation, with detection module 64 illustrated schematically. The flow cell may have channels arranged in a plane and forming singulator 72. The singulator, whether or not formed by a flow cell, may include an alignment region 202 in which droplets 104 are marshaled into single file, optionally gradually as the droplets travel to channel junction 106. The singulator, whether or not formed by a flow cell, also may include a spacing region 204 in which the distance between single-file droplets is increased, optionally progressively as the droplets travel away from channel junction 106 toward detection channel 74.

FIG. 7 shows how streams of fluid may be combined with one another by singulator 72. A stream 206 of droplet-containing fluid 102 provided by an emulsion may be directed to channel junction 106 by sample inlet channel 126. One or more streams 208*a*, 208*b* of spacing fluid may be directed to the channel junction by one or more spacing-fluid inlet channels 128*a*, 128*b*. A combined stream 210 of droplet-containing fluid 102 and spacing fluid may be created at channel junction 106 and directed to detection channel 74 by spacing channel 130. The combined stream may be directed through the detection channel to an outlet channel 212, which may extend to outflow port 178 of flow cell 170 (also see FIGS. 3 and 6).

Droplets 104 are shown as spherical in FIG. 7 to simplify the presentation. However, the droplets may be deformed, such as elongated in the direction of flow (e.g., by viscous forces), as each droplet passes through the singulator, particularly at positions where the cross-sectional dimension of the channels is smallest. The diameter of a droplet, as used herein, is defined for the droplet when substantially undeformed (i.e., spherical), whether or not the droplet ever actually assumes that shape, unless specified otherwise.

Cross-sectional channel dimensions are described herein using the terms diameter, width, and/or depth. The diameter of a channel is the average cross-sectional dimension measured orthogonal to the long axis of the channel, at a given position(s) along the channel. The width of a channel is (a) the cross-sectional dimension of a channel measured orthogonal to the long axis of the channel and parallel to a specified plane (e.g., the plane of a flow cell, or the plane defined by a plurality of channels that meet at a channel junction), at a given position(s) along the channel; and/or (b) the maximum cross-sectional dimension measured orthogonal to the long axis of the channel at a given position(s) along the channel. The depth of a channel is the cross-sectional dimension orthogonal to the channel's width and local long axis, at a given position(s) along the channel. If a channel has a circular cross-section at a given position, the channel's diameter, width, and depth are equal to one another at that position. If the channel has an elongated cross-section at a given position, the channel's diameter has a value that is intermediate the respective values for the channel's width and depth. A channel's long axis follows the path of the channel, and thus may be linear or nonlinear.

Alignment region 202 may be provided by at least a portion of sample inlet channel 126 that tapers in a downstream direction toward channel junction 106 (see FIGS. 6 and 7). The taper may be a taper in width, measured parallel to a plane defined by singulator 72, in depth measured orthogonal to the plane, and/or in diameter. The taper may define any suitable angle of taper with respect to the long axis of the sample inlet channel. The angle of taper may be constant, to produce a linear taper, or may vary, to produce an angle of taper that increases or decreases toward channel junction 106. The angle of taper may, for example, be less than about 10, 8, 6, 5, 4, 3, or 2 degrees, and/or an average of greater than about 0.5, 1, or 2 degrees, among others, with the value for the angle representing a constant angle of taper or an average angle of taper. In some embodiments, the angle of taper may be about 0.5-10, 1-5, or 1.5-3 degrees, among others, with the value for the angle representing a constant angle of taper or an average angle of taper. The angle of taper selected may be a compromise between a relatively smaller angle of taper, which may be advantageous as being less likely to damage droplets, and a relatively larger angle of taper, which allows the sample inlet channel to be shorter and thus provide less flow resistance and take up less real estate.

The alignment region may have any suitable length and cross-sectional dimensions. The length of the portion (or all) of sample inlet channel 126 that tapers may be at least about 5, 10, 15, or 20 times the minimum width, depth, diameter, and/or cross-sectional dimension of the sample inlet channel near or at channel junction 106. A relatively longer length for the tapered portion of the sample inlet channel may be advantageous as less likely to fragment/fuse droplets. The minimum diameter, width, and/or depth of the sample inlet channel may be less than twice the average diameter of the droplets. In some embodiments, this minimum diameter may substantially match the average diameter of droplets 104. For example, the minimum diameter, width, and/or depth of the sample inlet channel may be no more than about 50%, 25%, 20%, or 10% larger (or smaller) than the average diameter of the droplets, and/or may be within about 50%, 25%, 20%, or 10% of the average diameter of the droplets. The maximum diameter, width, and/or depth of the sample inlet channel may be more than twice the average diameter of the droplets, such at least about 3, 4, or 5 times the average diameter of the droplets.

FIG. 7 illustrates how alignment region 202 may utilize a gentle taper to gradually align droplets 104 with one another in single file upstream of channel junction 106. The droplets are arranged randomly in at least two dimensions, with three or more droplets being present at single longitudinal positions of the channel, in the widest portion of alignment region 202, and become aligned with the long axis of the channel as the droplets approach channel junction 106.

Each spacing-fluid inlet channel 128a, 128b may form any suitable angle 214 with sample inlet channel 126 and/or any suitable angle 216 with one another as the channels extend to channel junction 106 (see FIG. 6). The value for each angle is defined between the respective long axes of a pair of channels. Angle 214 may, for example, be 90 degrees or less than 90 degrees, such as less than about 60, 50, 40, or 30 degrees, among others. Angle 216 may, for example, be greater than 180 degrees, about 180 degrees, or less than 180 degrees, such as less than about 120, 100, 90, 80, 70, 60, or 50 degrees, among others. A smaller value for angle 214 and/or angle 216 allows fluid streams to combine with one another more gently, which may reduce damage to droplets.

Spacing region 204 of singulator 72 may be defined by spacing channel 130 (see FIGS. 6 and 7). The spacing region may increase the distance between adjacent droplets relative to their separation, if any, at the end of alignment region 202, and/or may increase the distance between adjacent droplets progressively as the droplets travel along spacing channel 130 toward the detection channel.

Spacing channel 130 may have any suitable properties. The spacing channel may taper toward detection channel in diameter, width, and/or depth. For example, the width may decrease while the depth remains substantially constant. The taper may be constant or variable. For example, the taper may decrease toward the detection channel, as shown in the depicted embodiment, which may damage droplets less than a constant or increasing taper. In some embodiments, the taper may provide a substantially constant acceleration of the droplets. Spacing channel 130 may have a width (e.g., a maximum width) adjacent channel junction 106 that is about the same as the combined widths of sample inlet channel 126 and spacing-fluid inlet channels 128a, 128b adjacent channel junction 106. The spacing channel may have a minimum width and/or minimum diameter where the spacing channel joins detection channel 74. The minimum width and/or minimum diameter may be the same as the average width and/or average diameter of the detection channel, or the detection channel may decrease in size cross-sectionally as it extends from the spacing channel. The minimum width and/or minimum diameter of the spacing channel may correspond to the average diameter of droplets 104, such as being within about 50%, 25%, 20%, or 10% of the average diameter. The maximum width of the spacing channel may be at least about 3, 4, or 5 times its minimum width. The length of the spacing channel, indicated at 218 in FIG. 7, may be at least about 10, 15, or 20 times its minimum width and/or at least about 3, 4, or 5 times its maximum width.

Detection channel 74 may have any suitable structure and properties. The detection channel may, for example, be continuous with spacing channel 130. Detection channel 74 may have a constant or varying width, depth, and/or diameter. In some embodiments, the width and depth may be within about 20% or 10% of one another. The detection channel may have a length, indicated at 220, that is at least about 3, 4, 5, 6 or 8 times its width, depth, and/or diameter and/or at least about 3, 4, 5, 6, or 8 times the average diameter of droplets 104. The detection system may be configured and operated such that at least one droplet 104 is substantially always present in the detection channel while droplet-containing fluid is passing through flow cell 170, to minimize pulsing. The detection channel and/or sample inlet channel 126 may define the minimum width and/or minimum diameter of the channels of singulator 72, flow cell 170, and/or of the flow path from the open end of tube 114 to a pump that draws emulsion-containing fluid and spacing fluid through singulator 72. Accordingly, outlet channel 212 may increase in width and/or diameter immediately downstream from the detection channel, to minimize the resistance to fluid flow created by the flow cell outside singulator 72.

Detection module 64 of detection system 150 is shown schematically in FIG. 7, to illustrate an exemplary detection zone 222 of detection channel 74 from which optical radiation may be detected. Detection zone 222 may be irradiated with light (ultraviolet, visible, and/or infrared) generated by at least one light source 90. Optical radiation (ultraviolet, visible, and/or infrared) from the detection zone may be detected with at least one detector 88. The optical radiation detected may be a deflected portion of the light used for irradiation and/or may be photoluminescence induced by irradiation, among others. The detection zone may represent any suitable portion of the length of detection channel 74, such as less than about 50%, 20%, 10%, or 5% of the length, and/or may be shorter, measured along the long axis of the detection channel, than the average diameter of the droplets.

FIG. 6 show further exemplary aspects of flow cell 170 and/or singulator 72. Spacing fluid may flow from spacing-fluid port 176 to spacing-fluid inlet channels 128a, 128b via a single inflow channel 224. The inflow channel may branch to form spacing-fluid inlet channels 128a, 128b, or the inlet channels may be fed with spacing fluid via respective spacing-fluid ports of the flow cell. Each spacing-fluid inlet channel 128a, 128b may taper as it extends to channel junction 106. The angle of taper with respect to the long axis of the corresponding channel, may, for example, be less than about 5, 4, 3, 2, or 1 degree(s), among others. Detection system 150 may be designed and operated such that the velocity of droplets entering channel junction 106 substantially matches the velocity of spacing fluid entering the channel junction, to minimize damage to droplets that would be produced by unmatched velocities. For example, the velocities may be within about 50% or 25% of one another.

FIG. 8 shows an exemplary construction of flow cell 170. The flow cell may include layers 230, 232 (interchangeably termed substrates) that are bonded to one another face-to-face. The layers may have the same thickness or may be different in thickness, as shown in FIG. 8. The layers may be transparent to optical radiation, such as visible light, and may be formed of any suitable transparent material, such as glass or plastic. Channels of the flow cell, such as channels 126, 128a, 128b, 130, and 74, may be formed integrally with one another by the layers. More particularly, each channel may be created cooperatively by a groove 234 defined in a face of layer 230 and a corresponding groove 236 defined in a face of layer 232. The grooves may be aligned with one another when the layers are bonded, to form the channels. The grooves may have the same depth as one another or may differ in depth.

Grooves 234, 236 may be formed by etching the layers. A face of each layer may be masked with an-etchant resistant mask. Non-masked regions of each face may be etched isotropically with an etchant, such as an acid (e.g., hydrofluoric acid), to create the grooves. The depth of each groove may be substantially constant, as shown in FIG. 8, or may vary by etching some portions of the groove longer (e.g., by using two etching steps). Accordingly, the depth of the various channels of the flow cell, measured orthogonal to the plane of the flow cell, may be the same, while the widths, measured parallel to the plane, may vary. For example, FIGS. 9 and 10 show exemplary cross-sectional geometries of detection channel 74, which may be nearly cylindrical, and flush channel 172, which may have a width that is at least two or three times its depth.

FIG. 8 also shows sample port 174 and flushing port 180. Each port of the flow cell may be a cylindrical hole formed in one of the layers, such as oriented orthogonal to the plane of the flow cell, and intersecting one of grooves 234, 236. In the depicted embodiment, each port is defined by thicker layer 230 and intersects groove 234, but in other embodiments, one or more ports may be defined by each layer. The ports may be formed by any suitable procedure, such as ultrasonic drilling. Each port may have a diameter that matches the width of a channel intersected by the port.

The internal channels of the flow cell may be connected to the rest of a fluid transporter's channel network via ports of the flow cell. For example, the end of a tube 238 of the channel network may be placed into each port and sealed using a face seal 240 to prevent leakage around the port.

FIG. 8 illustrates an exemplary arrangement for detection module 64. Flow cell 170 provides two sides 242, 244 that permit optical communication with detection zone 222. The sides face away from one another, and may be planar and parallel to one another. The detection zone may be irradiated with light from light source 90 through one of the sides (e.g., side 244), and light may be received from the detection zone via one or both sides 242, 244. For example, in the depicted embodiment, irradiation light from light source 90 passes through beam splitter 246 and side 244, to irradiate the detection zone. Deflected light may be detected by a deflection detector 88a via side 242. (Deflected light may be light that has been reflected, refracted, and/or scattered by droplets.) Light emitted from the detection zone may be detected by a photoluminescence detector 88b via side 244. Further aspects of detection systems for detecting deflected light and emitted light from droplets are described in the patent documents listed above under Cross-References, which are incorporated herein by reference, including U.S. patent application Ser. No. 15/394,605; and U.S. patent application Ser. No. 15/394,624.

A singulator and detection channel, optionally both provided by the same flow cell, may include any combination of the following novel features in the context of a droplet detection system, as disclosed herein. The detection channel may be in close proximity to a spacing channel of the singulator, which can provide for maximal separation of droplets at the point of detection. The detection channel may be provided by a flow cell having two sides available for photoluminescence detection and deflection detection as droplets pass through the flow cell. A tapered sample inlet "funnel" may gradually marshal droplets into single file prior to being spaced from one another. Channel geometries may match flow speeds of sample and spacing fluid at the confluence region, to minimize stress on droplets as they enter a spacing channel. The spacing channel may have a tapered profile between the confluence region and the detection channel, with a geometry that provides for gradual and approximately constant acceleration of droplets. The acceleration profile may be configured to minimize the stress on droplets to avoid damage, to allow droplets to have a stable shape by the time they are detected in the detection channel, and to permit droplets to pass through the detection channel at higher rates than previously possible. The singulator and detection channel may offer a low total fluidic resistance that makes it possible to operate a transporter with a suck-through design, using a pump applying suction downstream of the detection channel, and a spacing-fluid source at ambient pressure, without significant outgassing. Cylindrical ports of a flow cell may minimize carryover at the junction of the fluidic interface and flow cell.

IV. Suction Loading, Push-Through Detection System

This section describes an exemplary detection system 250 utilizing a two-phase approach for droplet detection. During a first phase, droplet-containing fluid 102 of an emulsion 58 is loaded into a fluid transporter 60 of the system by suction (see FIG. 11). In a second phase, fluid 102 is combined with spacing fluid 82 within a singulator 72 and pushed through a detection channel 74 (see FIG. 12). Detection system 250 may include any suitable combination of the components and features described above for detection systems 50, 100, and 150, although its two-phase approach for loading and push-through is fundamentally different from the single phase, suck-through approach of systems 100 and 150.

Detection system 250 has some similarity to detection system 150 and is drawn using the same conventions to show flow paths and fluid flow. System 250, like system 150, has a pair of pumps 78a, 78b to drive fluid into and within a channel network 70 that includes singulator 72 and detection channel 74. Also, the pump and the channel network may be primed with spacing fluid 82 beforehand to prepare fluid transporter 60 for emulsion processing. However, the pumps are utilized differently than in system 150.

Figure 11:
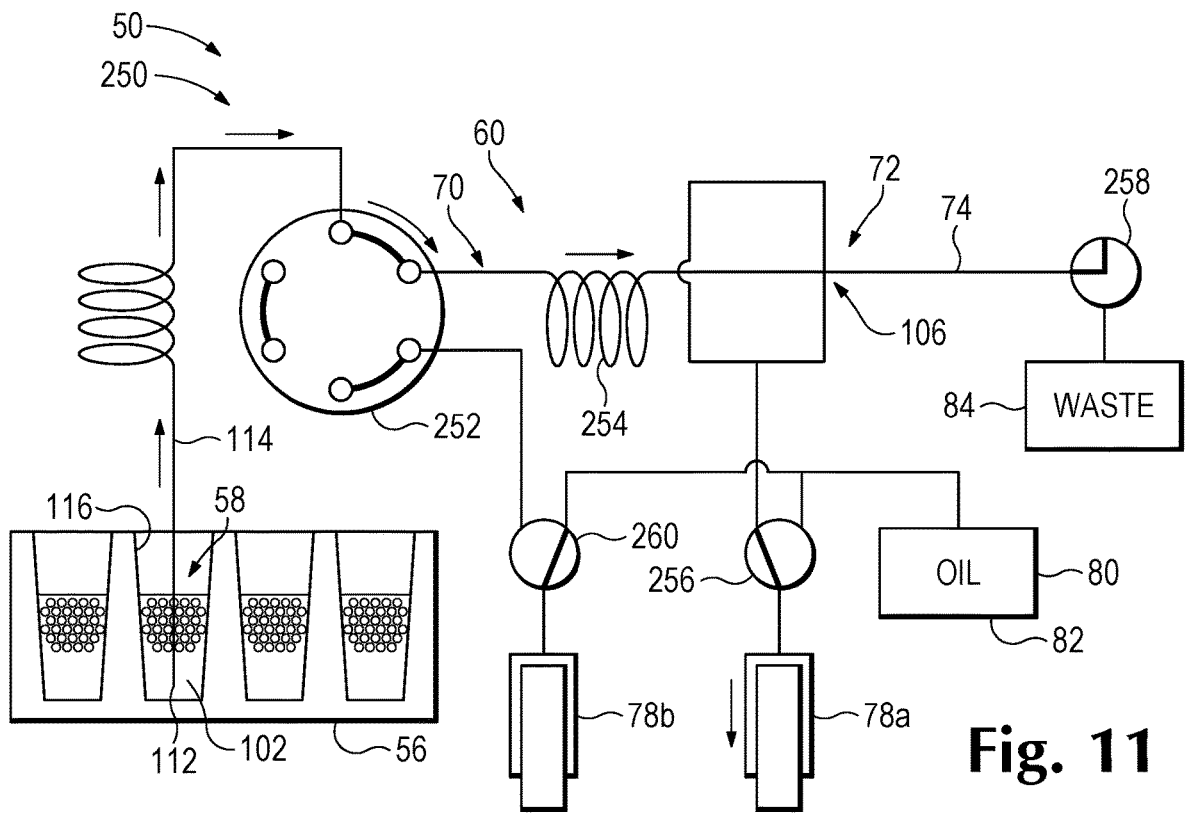
FIG. 11 is a schematic diagram of a fluid transporter and sample holder of another exemplary version of the system of FIG. 1, with the fluid transporter in a loading configuration for loading droplets into the transporter before the transporter is placed in a singulation/detection configuration that singulates and detects the loaded droplets, in accordance with aspects of the present disclosure.

FIG. 11 shows system 250 as droplet-containing fluid 102 is being drawn into channel network 70 in response to suction applied by pump 78a. In contrast to system 150, pump 78a is isolated from spacing-fluid reservoir 80 at this point, and thus the suction does not draw spacing fluid 82 from the reservoir into the channel network. The suction is transmitted to open end 112 of tube 114 via a flow path of channel network 70 that extends through a multi-port valve 252, a holding region 254, a channel junction 106 of singulator 72, and a three-port valve 256. Fluid 102 is drawn through valve 252 and into holding region 254, but not past the holding region. Accordingly, little or none of fluid 102 may be drawn through channel junction 106 during this loading phase. The capacity of holding region 254 may be sufficient to contain substantially the entire volume of emulsion 58. Accordingly, a majority of the emulsion may be loaded into holding region 254 using a flow path that does not include detection channel 74. Also, flow through the detection channel may be discouraged via an outflow valve 258 that blocks fluid flow from detection channel to a waste receptacle 84.

Pump 78b may or may not move fluid during the loading phase. In the depicted embodiment, pump 78b is connected to reservoir 80 via a valve 260 and may be idle or actively drawing spacing fluid 82 into the pump. However, in other embodiments, pump 78b may be configured to push fluid, such as spacing fluid 82, through valves 252 and 260, and onto the outside of tube 114 (such as via a sleeve), to rinse a protruding end region thereof, as described above for system 150, pump 78b, and sleeve 166 (see FIG. 3).

Figure 12:
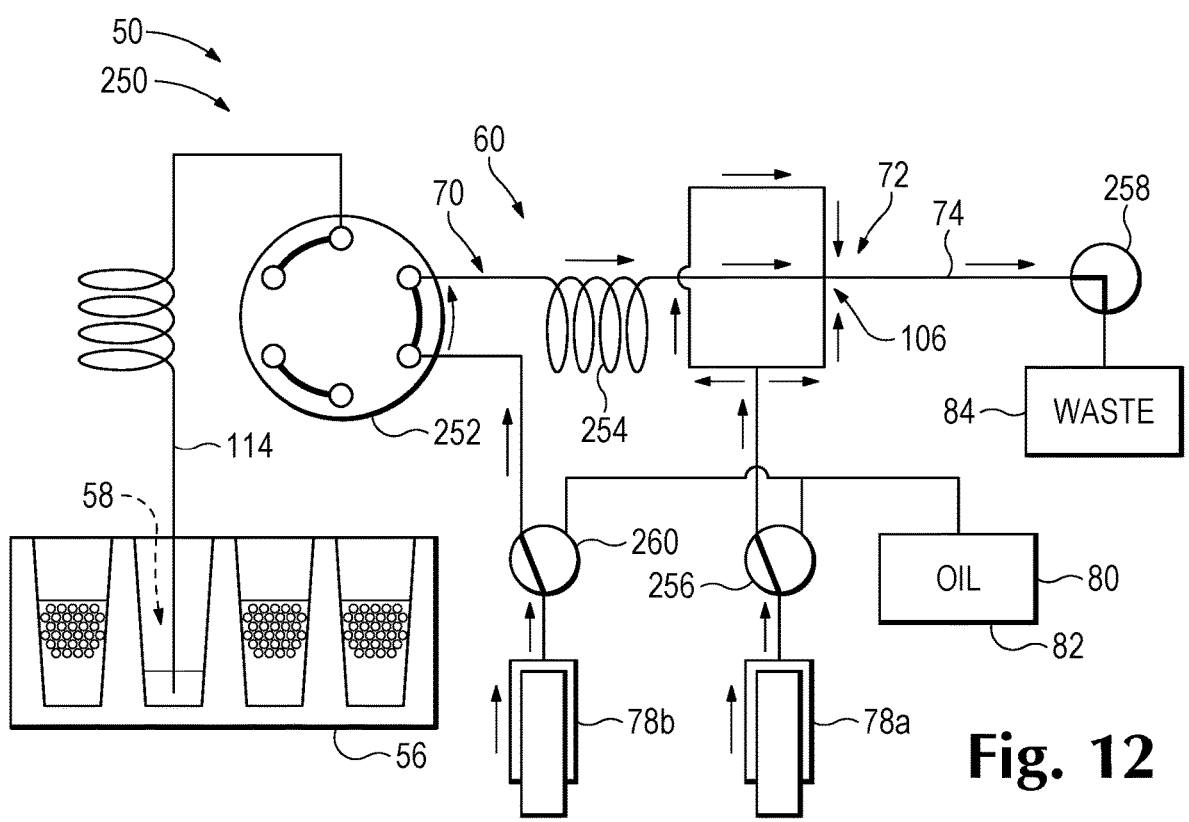
FIG. 12 is a schematic diagram of the system of FIG. 11 in the singulation/detection configuration that pushes loaded droplets and spacing fluid through a singulator and detection channel, in accordance with aspects of the present disclosure.

FIG. 12 shows system 250 as droplet-containing fluid 102 is being pushed from holding region 254 using positive pressure applied with pump 78b. The pump is in fluid communication with holding region 254 via valves 252 and 260, each of which has been adjusted relative to FIG. 11 to create the fluid communication. Valve 258 also has been adjusted to create fluid communication between holding region 254 and (vented) waste receptacle 84, which allows fluid 102 to pass through channel junction 106, detection channel 74, and valve 258, before entering the waste receptacle.

At the same time, pump 78a is applying positive pressure to channel network 70 with spacing fluid 82 that is being dispensed from the pump. The positive pressure urges spacing fluid to channel junction 106, such that a stream of fluid 102 from a sample inlet channel is combined with at least one stream of the spacing fluid from one or more spacing-fluid inlet channels at the junction, as described above for systems 100 and 150. The resulting combined stream is conveyed through detection channel 74, where a signal is detected from droplets, and is directed downstream to waste receptacle 84.

V. Droplet Disaggregation

Figure 13:
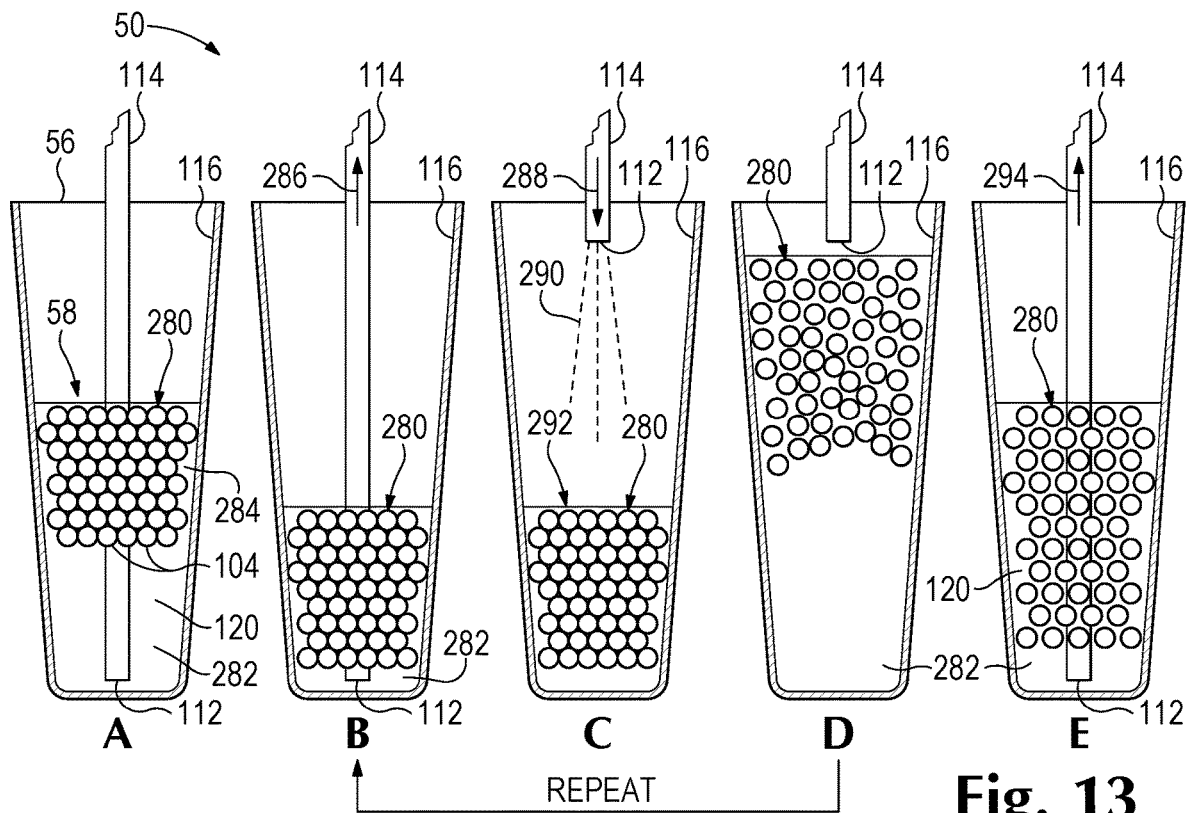
FIG. 13 is a partially sectional, fragmentary view of a series of configurations of a well, an emulsion including aggregated droplets, and a fluid transporter during performance of an exemplary droplet disaggregation routine as part of a method of droplet detection, in accordance with aspects of the present disclosure.
Figure 14:
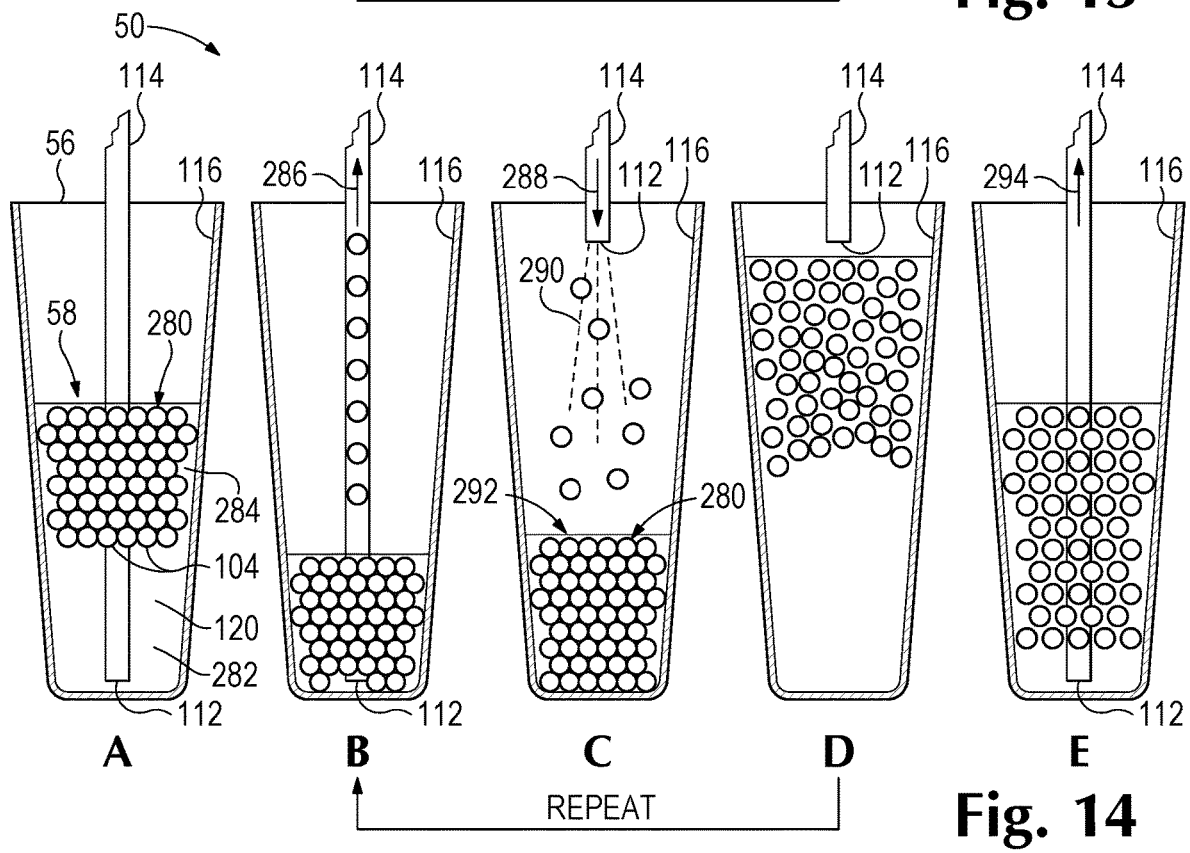
FIG. 14 is a partially sectional, fragmentary view of a series of configurations of a well, an emulsion including aggregated droplets, and a droplet transporter during performance of another exemplary droplet disaggregation routine as part of a method of droplet detection, in accordance with aspects of the present disclosure.

This section describes exemplary methods of, and systems for, droplet detection that include or utilize a droplet disaggregation routine (also called a disaggregation method and/or a droplet rinsing routine); see FIGS. 13 and 14. The method/routine steps disclosed in the section may be performed in any suitable order and combination, and may be combined with any other suitable steps disclosed elsewhere in the present disclosure. The methods/routines of this section may be performed by any suitable detection system, including any of the detection systems of the present disclosure (e.g., systems 50, 100, 150, and/or 250) with any suitable combination of components and features of these systems.

The droplet detection systems disclosed herein may be utilized to transport a bulk phase emulsion from a well into a microfluidic detection channel, from which a signal is detected while droplets of the emulsion pass serially through a detection zone of the channel. For these systems to be most effective, the emulsion should be transported from the well to the detection channel smoothly, efficiently, and predictably. However, some emulsion formulations and processing steps can cause droplets to have affinity for one another. For example, droplets having a skin, such as a proteinaceous skin including a skin-forming protein (e.g., a bulk protein such as a serum albumin), at the interface between each droplet and the continuous phase of the emulsion, sometimes stick to one another (also called clumping) to form a droplet aggregate. This tendency for the droplets to stick to one another can be exacerbated by heating the droplets to at least 50, 60, 70, 80, or 90 degrees Celsius (e.g., while contained in a well), such as when the droplets are thermally cycled, to encourage amplification (e.g., via a polymerase chain reaction and/or a ligase chain reaction). Storing the droplets, such as before or after heating, can also promote aggregation in a time-dependent fashion. Further aspects of creating a droplet skin and suitable skin-forming proteins are described in U.S. Patent Application Publication No. 2011/0217712 A1, which is incorporated herein by reference.

Aggregated droplets can reduce the efficiency and accuracy of droplet detection for several reasons. First, aggregated droplets are more difficult to aspirate efficiently with a fluid transporter. Sample utilization may be lower: aggregated droplets may be left behind in the well due to incomplete pickup. A substantial fraction of the droplets may remain behind in the well, such as on a side wall thereof, as one or more droplet clumps, after the majority of the emulsion's carrier liquid has been aspirated from the well. As a result, fewer droplets pass through the detection channel, which wastes droplets and reduces the accuracy of an assay performed with the droplets. Second, aggregated droplets that are aspirated as droplet clumps may clog channels within the detection systems, which may reduce throughput, require transporter servicing, and/or create greater risks of cross-contamination upstream of the detection channel of a fluid transporter when detecting droplets from a series of different emulsions. Third, droplets of a given emulsion may take longer to pass through the detector: the droplets may stream through the detection channel with multiple breaks. Fourth, flow rate through the detection channel may be more varied and droplets may be less regularly spaced, which leads to higher variations in detected droplet size and a decrease in measurement accuracy. The presence of a droplet aggregate(s) in the well may cause droplets of an emulsion to enter the transporter unevenly and unpredictably, which, in turn, can cause the spacing between droplets, the velocity of droplets, and the shape/deformation of droplets to fluctuate substantially for a given emulsion. As a result, each emulsion can take longer to read and the data collected may be less accurate.

The disaggregation routine disclosed herein, as a part of droplet detection method, can make a droplet pack more uniform, in order to reduce read time, increase sample utilization, and minimize the impact of flow variations on data quality. The routine may be performed in a method of reading droplets in a digital PCR assay. A particular configuration in which the method may be applicable includes a polymer well holding a biological sample contained in aqueous droplets surrounded by an oil continuous phase, and a hollow needle is used for aspirating droplets into a channel network including a singulator and a microfluidic detection channel. The end of the needle is placed into the emulsion; the tip of the needle is preferably within a short distance (e.g., 100-500 or 150-300 micrometers) above the bottom of the well, and then fluid is aspirated from the well into the needle and then dispensed back into the well, one or more times, as described in more detail below.

FIG. 13 shows exemplary configurations (panels A-E) of a droplet detection system 50 that may be produced while performing an exemplary droplet disaggregation routine on an emulsion 58 including droplets 104 surrounded (e.g., encapsulated) by a liquid continuous phase, namely, immiscible carrier liquid 120. The emulsion may be contained by a well 116, which may be a member of a multi-well array created by a sample holder 56 (e.g., a sample holder formed of polymer).

The routine may be performed with droplets that are buoyant, as shown, or that sink in the carrier liquid. In any case, the emulsion may include a pack 280 of droplets in which the droplets are packed together, such as closely packed. The pack may be a buoyant pack located at the top of the emulsion or a sunken pack located at the bottom of the emulsion. Droplets of the pack may have an affinity for one another, which may cause at least a subset of the droplets of the pack to stick together to form one or more aggregates. The affinity may be produced by interactions between surface components of the droplets. During thermal cycling, the top layer of the droplet pack may become sticky, which can have the adverse effects described above. In exemplary embodiments, the total volume of the emulsion may be about 10-100, 20-80, 30-70, or 40-60 μL, among others.

Only a subset of the droplets may include a target, such as a nucleic acid target. The subset may contain an amplicon corresponding to the target, and produced by amplification within the droplets. Amplification may be promoted by heating the droplets.

Carrier liquid 120 may be distributed between a substantially droplet-free volume portion 282 of the emulsion, which may underlie (or overlie) pack 280 and an interstitial volume portion 284 among droplets 104 within pack 280. The emulsion may have any suitable ratio of volume portion 282 to volume portion 284, such as greater than one, about one, or less than one, among others. In exemplary embodiments, the volume of droplets 104 plus interstitial volume portion 284 may, for example be about 40-80% or 50-70% of the total emulsion volume.

A tube 114 of fluid transporter 60 and well 116 may be moved relative to one another, to create contact between an open end 112 of the tube and emulsion 58 (see panel A of FIG. 13), as described elsewhere herein. The relative movement may position open end 112 in droplet-free volume portion 282. For example, in the depicted embodiment, open end 112 is positioned below pack 280, in a lower region of volume portion 282, near the bottom of well 116. Any movement of open end 112 and well 116 relative to one another in any of the methods and routines of this section may be effected by moving the open end, the well, or both. The bottom end of tube 114 may be stopped at a predetermined height above the bottom of the well, and below the droplet pack. The height, also called an elevation, may, for example, be about 50-1000, 100-500, or 150-300 micrometers above the bottom.

Fluid of emulsion 58 may be aspirated from well 116 via open end 112, indicated by a flow arrow 286 in panel B of FIG. 13. Droplet-free volume portion 282 may be aspirated selectively and/or substantially exclusively, and a majority (e.g., at least about 60%, 70%, 80% or 90%) of volume portion 282 may be aspirated. The volume of fluid aspirated may be a predetermined volume, which may be less than, about the same as, or greater than the volume of droplet-free volume portion 282 when aspiration is started.

At least a portion of the aspirated fluid may be dispensed back into well 116 via open end 112, indicated by a flow arrow at 288 and by dashed lines at 290, as shown respectively in panels C and D at the beginning and the end of dispensing. The step of dispensing disaggregates droplets of the emulsion (see panels D and E). (The droplets are shown as spaced from one another in panels D and E to indicate a more dispersed and/or less aggregated state.) The droplets may become closely packed again very quickly as the droplets reform pack 280, but do not stick to one another again, or at least not as stably, before they are aspirated into a fluid transporter for detection.

An elevation of open end 112 and well 116 relative to one another may be changed for the step of dispensing relative to the step of aspirating performed immediately before the step dispensing (compare panels B and D). For example, open end 112 may be withdrawn from the emulsion and positioned above an emulsion portion 292 remaining in well 116, and in vertical alignment with the well and/or emulsion portion 292. Open end 112 may be separated from the top of emulsion portion 292, and by any suitable distance, such as at least about 2, 3, 4, or 5 millimeters, among others.

Fluid may be dispensed at a higher flow rate than fluid was aspirated in the preceding step, and/or the step of dispensing may have a shorter duration than the step of aspirating. Accordingly, the fluid may be ejected forcefully from open end 112 and showered onto the fluid in the well by the step of dispensing, to encourage disaggregation of droplets.

A larger volume of fluid may be dispensed than was aspirated (compare panels A and D). The fluid dispensed may be a first volume of emulsion that was aspirated, plus a second volume of non-emulsion fluid from fluid transporter 60. The ratio of the first volume to the second volume may, for example, be about 0.25-1.0, 0.5-1.0, 0.5-1.5, or 1.0-2.0, among others. The non-emulsion fluid may be transporter fluid present in tube 114 (and other channels of the transporter) at the start of the disaggregation routine. The non-emulsion fluid may be miscible with the carrier liquid of the emulsion, and immiscible with the droplets. The non-emulsion fluid may be spacing fluid (see Sections I and II).

The step of aspirating followed by the step of dispensing may be repeated as a cycle any suitable number of times, which may disaggregate sticky droplets more thoroughly. However, after the first cycle of aspirating and dispensing, the volumes of fluid aspirated and dispensed may be the same as one another, to avoid diluting the emulsion excessively with transporter fluid and/or overfilling the well.

After the steps of aspirating and dispensing, droplet-containing fluid 102 may be aspirated from well 116 with tube 114 and transported through a detection channel of the system (indicated by a flow arrow at 294) (see panel E of FIG. 13). To aspirate the fluid from the well, open end 112 may be positioned at a predetermined height near the bottom of well 116, as in panel B, and substantially droplet-free fluid may be aspirated from the well first, to reach the configuration of panel E, and then droplet-containing fluid may be aspirated into the transporter. (The droplets may be closely packed again at this stage, but less stuck to one another.) A signal may be detected from the droplets as they pass through the detection channel, as described elsewhere herein (e.g., see Section I and II).

FIG. 14 shows exemplary configurations (panels A-E) of a droplet detection system 50 that may be produced while performing another exemplary droplet disaggregation routine on emulsion 58. The routine of FIG. 14 is very similar to that of FIG. 13, except that a larger volume of fluid is aspirated from the well by the step of aspirating, such that droplets are aspirated once the droplet-free volume portion becomes substantially depleted (compare panel B of FIGS. 13 and 14). Also, since droplets are aspirated, they are also dispensed by the step of dispensing (compare panel C of FIGS. 13 and 14).

In some embodiments of the routines of FIGS. 13 and 14, vertical motion of open end 112 and well 116 relative to one another, and liquid displacement (aspiration and/or dispensing), may be performed at least partially in parallel. For example, the step of aspirating (panel B) may be performed, at least in part, as open end 112 and well 116 are being moved relative to one another vertically, to place the open end near the bottom of the well. Also or alternatively, the step of dispensing (panel C) may be performed at least in part while moving open end 112 and well 116 relative to one another vertically. Furthermore, aspiration of fluid in panel E can be performed, at least in part, while open end 112 and well 116 are being moved relative to one another vertically, to place the open end near the bottom of the well. In these embodiments, the routine can be performed more quickly, to increase throughput.

Figure 15:
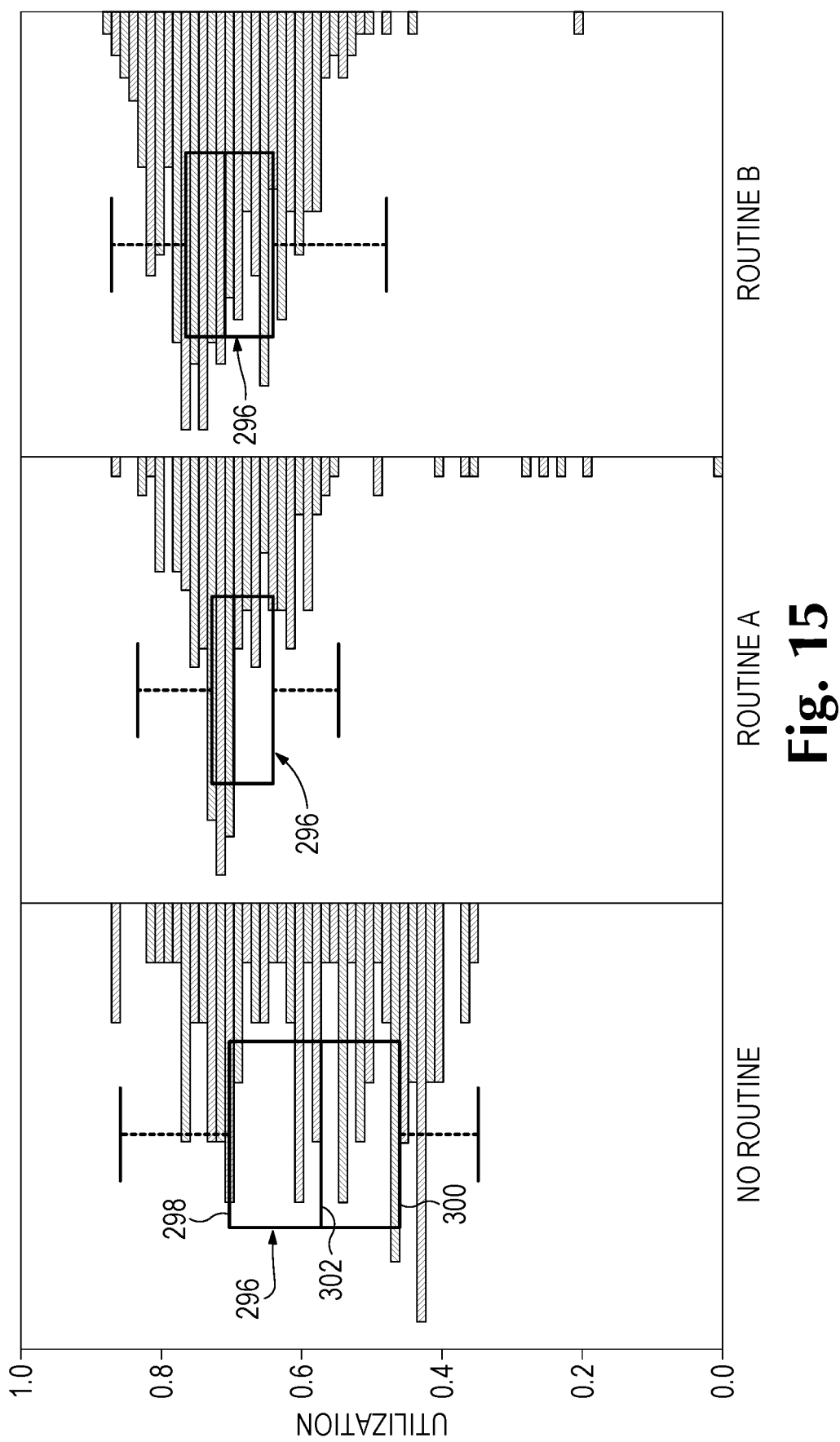
FIG. 15 is a series of histograms and corresponding box plots of droplet utilization after (A) no disaggregation routine, (B) the disaggregation routine of FIG. 14 (Routine A), and (C) the disaggregation routine of FIG. 13 (Routine B).
Figure 16:
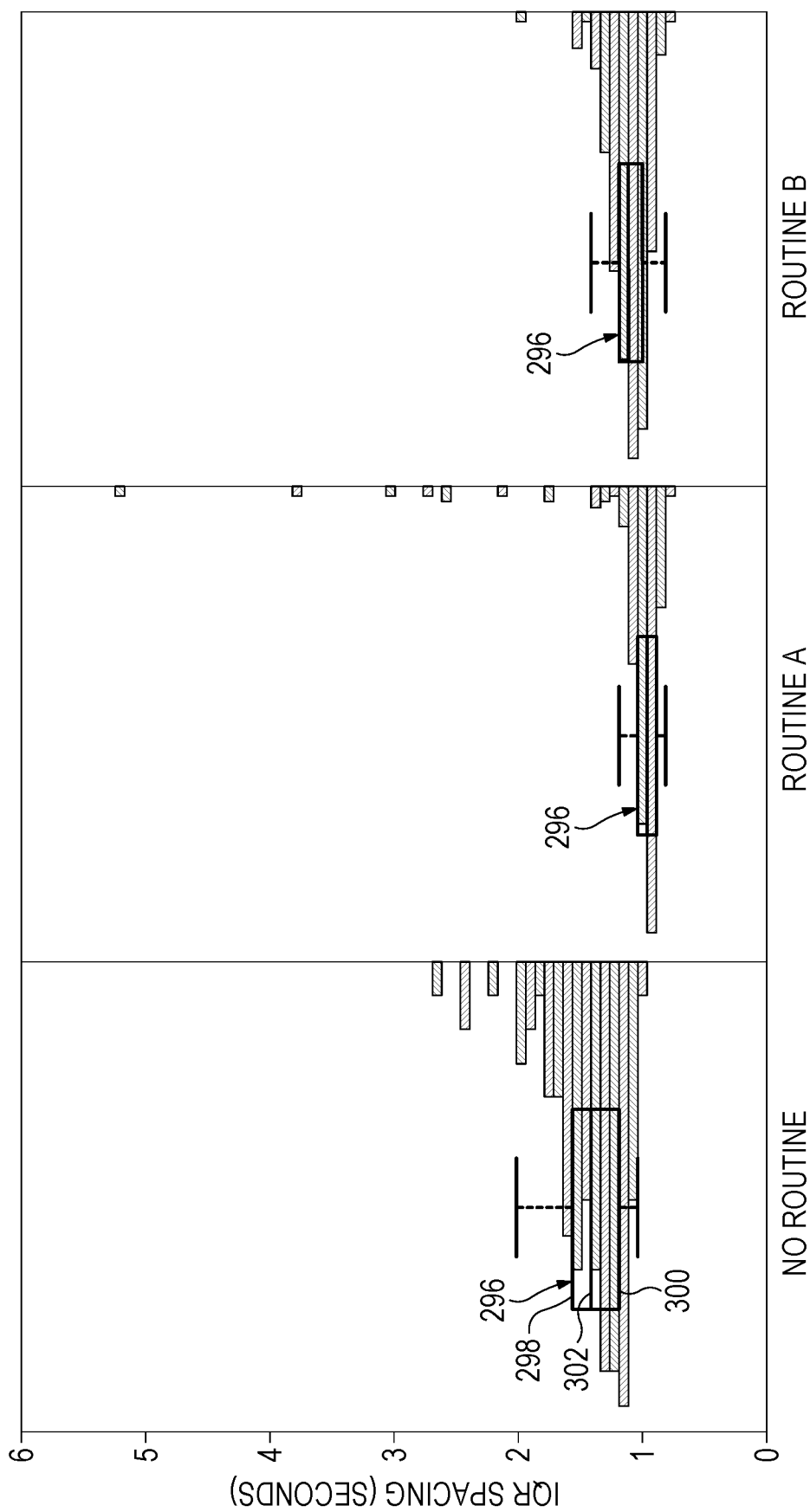
FIG. 16 is a series of histograms and corresponding box plots of the interquartile range of accepted droplet spacing with (A) no disaggregation routine, (B) the disaggregation routine of FIG. 14 (Routine A), and (C) the disaggregation routine of FIG. 13 (Routine B).

FIGS. 15 and 16 show histograms and box plots of data collected from emulsions using an embodiment of a detection method including no disaggregation routine, the routine of FIG. 14 ("Routine A"), or the routine of FIG. 13 ("Routine B"). Each histogram presents data collected from emulsions contained by a set of wells. Each bar of the histogram represents one or more of those wells, with the length of the bar corresponding to the number of wells represented. An interquartile box 296 is superimposed on each histogram. The top side 298 of the box is located at the third quartile of the distribution, the bottom side 300 of the box is located at the first quartile, and a line 302 inside the box is located at the median.

FIG. 15 shows data for utilization, which is the fraction of the dispersed volume (droplets) in each well that is aspirated and passed through the detection channel. The data demonstrate higher utilization when disaggregation Routines A and B are performed, before the droplets are picked up and detected, compared to no disaggregation routine. In other words, both routines reduced the fraction of droplets that remains behind in the well.

FIG. 16 shows data for the interquartile range of accepted droplet spacing for three sets of wells. Droplet spacing is the time gap between adjacent droplets normalized by the time of flight of the droplets through the detection zone. The range is lower for rinse Routines A and B compared to no routine, as expected for less clumpy, better dispersed droplets.

VI. Selected Embodiments

This section describes selected embodiments of the present disclosure as a series of indexed paragraphs.

Paragraph A1. A method of droplet detection, the method comprising: (a) generating a single-file stream of droplets in carrier liquid; (b) combining at least one stream of spacing fluid with the single-file stream of droplets in carrier liquid; (c) directing the combined streams to a detection channel using a spacing channel that tapers toward the detection channel, wherein a distance between adjacent droplets is increased as such droplets travel along the spacing channel toward the detection channel; and (d) detecting a signal from droplets passing through the detection channel, wherein, optionally, detecting a signal includes detecting light received from the detection channel and creating a signal representative of the light detected.

Paragraph A2. The method of paragraph A1, wherein the step of generating includes a step of passing droplets through an alignment region of a sample inlet channel, wherein a taper of the alignment region arranges droplets in single file before reaching a channel junction, and wherein the step of combining includes a step of combining at least one stream of spacing fluid with the single-file stream of droplets in carrier liquid at the channel junction.

Paragraph A3. The method of paragraph A2, wherein a maximum width of the alignment region is more than twice the average diameter of the droplets, and wherein a minimum width of the alignment region is about the same as the average diameter of the droplets.

Paragraph A4. The method of paragraph A2 or A3, wherein the step of combining includes a step of conveying spacing fluid to the channel junction in a pair of spacing-fluid inlet channels, and wherein the pair of spacing-fluid inlet channels form an angle of less than about 180, 120, or 90 degrees with one another as such inlet channels extend to the channel junction.

Paragraph A5. The method of paragraph A4, wherein each spacing-fluid inlet channel tapers toward the channel junction.

Paragraph A6. The method of any of paragraphs A2 to A5, wherein the step of directing the combined streams includes a step of directing the combined streams from the channel junction with a spacing channel defining an angle of taper that decreases as the spacing channel extends downstream toward the detection channel.

Paragraph A7. The method of any of paragraphs A2 to A6, wherein a velocity of spacing fluid entering the channel junction substantially matches a velocity of droplets entering the channel junction.

Paragraph A8. The method of any of paragraphs A1 or A7, wherein the step of generating includes a step of passing droplets through an alignment region defining a central axis and having a taper defining an average angle of taper with respect to the central axis of less than about 10, 7, or 5 degrees.

Paragraph A9. The method of any of paragraphs A1 to A8, wherein the step of combining includes a step of combining each stream of a pair of streams of spacing fluid with the single-file stream of droplets in carrier liquid, and wherein each stream of spacing fluid meets the single-file stream of droplets in carrier liquid at an angle of less than about 90, 60, or 45 degrees.

Paragraph A10. The method of any of paragraphs A1 to A9, wherein the step of detecting is performed while droplets pass through a substantially non-tapered detection channel.

Paragraph A11. The method of any of paragraphs A1 to A10, wherein a downstream end of the spacing channel transitions smoothly and seamlessly to an upstream end of the detection channel.

Paragraph A12. The method of any of paragraphs A1 to A11, further comprising a step of applying suction downstream of the detection channel, wherein the suction drives all fluid flow for the steps of generating, combining, directing, and detecting.

Paragraph A13. The method of any of paragraphs A1 to A12, wherein only a single pump drives fluid flow for the steps of generating, combining, directing, and detecting.

Paragraph A14. The method of any of paragraphs A1 to A13, wherein droplets are accelerated in the spacing channel, and, optionally, wherein droplets have a substantially constant acceleration in the spacing channel.

Paragraph A15. The method of any of paragraphs A1 to A14, wherein the spacing fluid is liquid and miscible with the carrier liquid.

Paragraph A16. The method of any of paragraphs A1 to A15, wherein the step of combining is performed at a channel junction where a plurality of channels meet one another, and wherein the plurality of channels and the detection channel are formed integrally with one another by a flow cell.

Paragraph A17. The method of paragraph A16, wherein the flow cell has a first side and a second side that face away from one another, and wherein the step of detecting includes a step of detecting photoluminescence received from the first side and deflected light received from the second side.

Paragraph A18. The method of any of paragraphs A1 to A17, wherein the method is performed with the detection system of any of paragraphs B1 to B25, C1 to C4, E1 to E6, and G1.

Paragraph A19. The method of any of paragraphs A1 to A17, wherein the method further comprises any step(s) of the method of any of paragraphs D1 to D17 and F1 to F19.

Paragraph B1. A detection system for droplets, comprising: (a) a channel network including a sample inlet channel, at least one spacing-fluid inlet channel, and a spacing channel that meet one another at a channel junction, and a detection channel in fluid communication with the channel junction via the spacing channel; (b) a spacing-fluid source connected to the channel network; (c) a detector configured to receive and detect light from the detection channel; and (d) one or more positive/negative pressure sources operatively connected to the channel network and configured to drive droplet-containing fluid from an emulsion source to the channel junction via the sample inlet channel, spacing fluid from the spacing-fluid source to the channel junction via the at least one spacing-fluid inlet channel, and droplet-containing fluid combined with spacing fluid from the channel junction and through the spacing channel and the detection channel; wherein the sample inlet channel tapers toward the channel junction to force droplets into single file before such droplets reach the channel junction, and wherein the spacing channel tapers toward the detection channel to progressively increase a distance between adjacent droplets as the adjacent droplets travel from the channel junction to the detection channel.

Paragraph B2. The detection system of paragraph B1, wherein the sample inlet channel, the at least one spacing-fluid inlet channel, the spacing channel, the channel junction, and the detection channel are formed integrally with one another by a flow cell.

Paragraph B3. The detection system of paragraph B2, wherein the flow cell includes a pair of layers bonded to one another, and wherein each layer defines a portion of the sample inlet channel, the at least one spacing-fluid inlet channel, the spacing channel, the channel junction, and the detection channel.

Paragraph B4. The detection system of paragraph B3, wherein the layers are formed of glass, and wherein the sample inlet channel, the at least one spacing-fluid inlet channel, the spacing channel, the channel junction, and the detection channel are formed by etching the glass before the layers are bonded to one another.

Paragraph B5. The detection system of any of paragraphs B2 to B4, wherein the detection channel has a depth measured orthogonal to a plane of the flow cell and a width measured parallel to the plane, and wherein the depth is within 50%, 30%, or 20% of the width.

Paragraph B6. The detection system of any of paragraphs B2 to B5, wherein the sample inlet channel has a site of minimum width, and wherein a depth of the alignment region at the site of minimum width is within 50%, 30%, or 20% of the minimum width.

Paragraph B7. The detection system of any of paragraphs B2 to B6, wherein the sample inlet channel, the at least one spacing-fluid inlet channel, the spacing channel, the channel junction, and the detection channel each have the same depth.

Paragraph B8. The detection system of any of paragraphs B2 to B7, wherein the flow cell defines a sample port at which droplet-containing fluid enters the flow cell, and a spacing-fluid port at which spacing fluid enters the flow cell.

Paragraph B9. The detection system of paragraph B8, wherein the flow cell defines a plane, and wherein each of the sample port and the spacing-fluid port is oriented transverse to the plane.

Paragraph B10. The detection system of paragraph B8 or B9, wherein the flow cell defines a flushing port at which fluid enters the flow cell, and a flushing channel extending from the flushing port to the sample port.

Paragraph B11. The detection system of paragraph B10, wherein the flushing port is connected to a source of positive/negative pressure that is configured to drive flushing fluid into the flow cell at the flushing port and through the flushing channel to the sample port and/or the sample inlet channel, after the step of detecting has been completed, and wherein, optionally, the flushing fluid is spacing fluid from the spacing-fluid source.

Paragraph B12. The detection system of any of paragraphs B1 to B11, where the sample inlet channel includes an alignment region defining a central axis and an angle of taper with respect to the central axis of less than about 10, 7, or 5 degrees.

Paragraph B13. The detection system of any of paragraphs B1 to B12, wherein each spacing-fluid inlet channel forms an angle of less than about 90, 60, or 45 degrees with the sample inlet channel adjacent the channel junction.

Paragraph B14. The detection system of any of paragraphs B1 to B13, wherein the at least one spacing-fluid inlet channel includes a pair of spacing-fluid inlet channels forming an angle of less than about 180, 120, or 90 degrees between one another adjacent the channel junction.

Paragraph B15. The detection system of any of paragraphs B1 to B14, wherein the spacing channel defines an angle of taper that decreases downstream toward the detection channel.

Paragraph B16. The detection system of any of paragraphs B1 to B15, wherein the spacing channel has a nonlinear taper.

Paragraph B17. The detection system of any of paragraphs B1 to B16, wherein the sample inlet channel and the detection channel have respective minimum widths that are within about 50%, 30%, or 20% of one another.

Paragraph B18. The detection system of any of paragraphs B1 to B17, wherein the detection channel has an average width that is about the same as the average diameter of the droplets.

Paragraph B19. The detection system of any of paragraphs B1 to B18, wherein the sample inlet channel has a minimum width adjacent the channel junction, and wherein an average width of the spacing channel is greater than the minimum width.

Paragraph B20. The detection system of any of paragraphs B1 to B19, wherein a width of the spacing channel at the channel junction is at least approximately equal to a combined width of the sample inlet channel and the at least one spacing-fluid inlet channel at the channel junction.

Paragraph B21. The detection system of any of paragraphs B1 to B20, wherein each spacing-fluid inlet channel tapers toward the channel junction.

Paragraph B22. The detection system of any of paragraphs B1 to B21, wherein the detection channel has a substantially uniform width.

Paragraph B23. The detection system of paragraph B22, wherein the detection channel has a length and a uniform width, and wherein the length is no more than about 20 or 10 times the uniform width.

Paragraph B24. The detection system of paragraph B23, wherein the spacing channel has a length over which a width of the spacing channel varies, wherein the detection channel has a uniform width, and wherein the length of the spacing channel is less than about 5, 4, 3, or 2 times the length of the detection channel.

Paragraph B25. The detection system of any of paragraphs B1 to B24, wherein the sample inlet channel, and/or the detection channel, has a minimum width, and wherein the spacing region of the spacing channel has a length over which a width of the spacing channel varies, and wherein the length is no more than about 20 times the minimum width.

Paragraph B26. The detection system of any of paragraphs B1 to B25, further comprising one or more limitations of the detection system of any of paragraphs C1 to C4, E1 to E6, and G1.

Paragraph C1. A detection system for droplets, comprising: (a) a flow cell including a sample inlet channel, at least one spacing-fluid inlet channel, and a spacing channel that meet one another at a channel junction, and a detection channel in fluid communication with the channel junction via the spacing channel, the channels being formed integrally with one another; (b) a spacing-fluid source; (c) a detector configured to receive and detect light from the detection channel; and (d) one or more positive/negative pressure sources operatively connected to the flow cell and configured to drive droplet-containing fluid from an emulsion source to the channel junction via the sample inlet channel, spacing fluid from the spacing-fluid source to the channel junction via the at least one spacing-fluid inlet channel, and droplet-containing fluid combined with spacing fluid from the channel junction and through the spacing channel and the detection channel.

Paragraph C2. The detection system of paragraph C1, wherein the flow cell has a first side and a second side that face away from one another, and wherein the detector includes a first detector configured to detect photoluminescence received from the first side of the flow cell and a second detector configured to detect deflected light received from the second side of the flow cell.

Paragraph C3. The detection system of paragraph C1, wherein the flow cell defines a sample port, a spacing-fluid port, a flushing port, an outflow port, and a flushing channel, wherein the sample port is in fluid communication with the channel junction within the flow cell via the sample inlet channel, wherein the spacing-fluid port is in fluid communication with the channel junction within the flow cell via the at least one spacing-fluid inlet channel, wherein the outflow port is in fluid communication with the channel junction within the flow cell via the spacing channel and the detection channel, and wherein the flushing port is in fluid communication with the sample port and the sample inlet channel within the flow cell via the flushing channel.

Paragraph C4. The detection system of any of paragraphs C1 to C3, wherein the at least one source of positive/negative pressure includes a source of positive/negative pressure configured to apply suction downstream of the detection channel to drive droplet-containing fluid and spacing fluid through the channel junction and the detection channel.

Paragraph C5. The detection system of any of paragraphs C1 to C4, further comprising one or more limitations of the detection system of any of paragraphs A1 to A17, B1 to B25, E1 to E6, and G1.

Paragraph D1. A method of droplet detection, the method comprising: (a) moving an open end of a tube and a well relative to one another to create contact between the open end and an emulsion held by the well, the emulsion including droplets surrounded by carrier liquid; (b) applying suction downstream of a detection channel, wherein the suction draws (i) droplet-containing carrier liquid from the well and into the tube via the open end, and through a channel junction and the detection channel, and (ii) spacing fluid through the junction and the detection channel, wherein a stream of the spacing fluid is combined with a stream of the droplet-containing carrier liquid at the channel junction upstream of the detection channel; and (c) detecting a signal from droplets passing through the detection channel wherein, optionally, detecting a signal includes detecting light received from the detection channel and creating a signal representative of the detected light.

Paragraph D2. The method of paragraph D1, wherein the step of moving includes a step of moving the well while the open end of the tube remains stationary.

Paragraph D3. The method of paragraph D1 or D2, wherein a top of the well is sealed by a sealing member, further comprising a step of piercing the sealing member, optionally with the tube, to gain access to the well.

Paragraph D4. The method of any of paragraphs D1 to D3, wherein only a single pump drives fluid flow through the channel junction during the step of applying suction.

Paragraph D5. The method of any of paragraphs D1 to D4, wherein the step of applying suction draws droplet-containing carrier liquid to the channel junction in a sample inlet channel having a tapered alignment region, and draws spacing fluid to the channel junction in a pair of spacing-fluid inlet channels that each meet the sample inlet channel at the channel junction.

Paragraph D6. The method of any of paragraphs D1 to D5, wherein the spacing fluid is liquid and miscible with the carrier liquid of the emulsion and immiscible with the droplets.

Paragraph D7. The method of any of paragraphs D1 to D6, wherein the droplet-containing carrier liquid follows a flow path extending from the open end of the tube to a position downstream of the detection channel, and wherein a tapered alignment region of a sample inlet channel and/or the detection channel defines a minimum width of the flow path.

Paragraph D8. The method of any of paragraphs D1 to D7, wherein the droplet-containing carrier liquid follows a valve-less flow path extending from the open end of the tube to a position downstream of the detection channel.

Paragraph D9. The method of any of paragraphs D1 to D8, wherein the step of applying suction is performed with a pump and includes a step of collecting fluid received from the detection channel in a holding region located downstream of the detection channel, further comprising a step of pushing the collected fluid from the holding region to a waste receptacle with the pump after the step of detecting has been completed.

Paragraph D10. The method of any of paragraphs D1 to D9, wherein the channel junction and the detection channel are formed integrally with one another by a flow cell, wherein the flow cell defines a sample port, a spacing-fluid port, and a flushing port, wherein the step of applying suction draws droplet-containing carrier liquid of the emulsion into the flow cell at the sample port and spacing fluid into the flow cell at the spacing-fluid port, further comprising a step of driving flushing fluid from the flushing port to the sample port after the step of detecting has been completed, the flushing fluid optionally having the same composition as the spacing fluid.

Paragraph D11. The method of paragraph D10, wherein the step of driving flushing fluid includes a step of driving flushing fluid from the flushing port through the junction and the detection channel.

Paragraph D12. The method of any of paragraphs D1 to D11, further comprising a step of arranging droplets of the droplet-containing carrier liquid in single file as such droplets approach the channel junction, and a step of increasing a distance between adjacent droplets as the adjacent droplets travel from the channel junction to the detection channel.

Paragraph D13. The method of paragraph D12, wherein the step of arranging droplets includes a step of passing droplets through an alignment region of a sample inlet channel, and wherein the alignment region tapers toward the channel junction.

Paragraph D14. The method of paragraph D13, wherein the step of increasing a distance between adjacent droplets includes a step of passing the droplets through a tapered spacing channel on a flow path between the channel junction and the detection channel.

Paragraph D15. The method of any of paragraphs D1 to D14, wherein the step of applying suction is performed with a source of suction and produces a pressure differential of less than 2 psi (13.8 kPa) between the open end of the tube and the source of suction.

Paragraph D16. The method of any of paragraphs D1 to D15, wherein the channel junction is in fluid communication with a reservoir holding spacing fluid, and wherein the reservoir remains vented during the step of applying suction.

Paragraph D17. The method of any of paragraphs D1 to D16, wherein the step of applying suction generates a first stream of the droplet-containing carrier liquid and a second stream of the spacing fluid, and wherein the velocity of the first stream matches the velocity of the second stream at the channel junction.

Paragraph D18. The method of any of paragraphs D1 to D17, wherein the method is performed with the detection system of any of paragraphs B1 to B25, C1 to C5, E1 to E6, and G1.

Paragraph D19. The method of any of paragraphs D1 to D17, wherein the method further comprises any step(s) of the method of any of paragraphs A1 to A17 and F1 to F19.

Paragraph E1. A system for droplet detection, comprising: (a) a well to hold an emulsion including droplets surrounded by a carrier liquid; (b) a tube having an open end, the well and the open end being movable relative to one another to create contact between the open end and the emulsion; (c) a channel junction; (d) a detection channel; (e) a detector configured to detect a signal from droplets passing though the detection channel, wherein, optionally, the detector is configured to receive and detect light from the detection channel and create a signal representative of the detected light; and (f) a source of suction located downstream of the detection channel and configured to apply suction that drives (i) droplet-containing carrier liquid from the well and into the tube via the open end, and through the channel junction and the detection channel, and (ii) spacing fluid through the channel junction and the detection channel, wherein a stream of the spacing fluid is combined with a stream of the droplet-containing carrier liquid at the channel junction upstream of the detection channel.

Paragraph E2. The system of paragraph E1, further comprising a conveyor configured to drive movement of the well vertically while the open end of the tube remains stationary.

Paragraph E3. The system of paragraph E1 or E2, wherein the source of suction is a source of positive/negative pressure including a pump.

Paragraph E4. The system of paragraph E3, wherein the detection channel is in fluid communication with the pump via a holding region for collecting fluid received from the detection channel, and wherein the pump is configured to push collected fluid from the holding region to a waste receptacle by application of positive pressure after application of the suction.

Paragraph E5. The system of any of paragraphs E1 to E4, further comprising a reservoir to supply spacing fluid to the channel junction, wherein the reservoir is vented to ambient pressure.

Paragraph E6. The system of any of paragraphs E1 to E5, wherein the tube is in fluid communication with the channel junction via tubing that is more flexible than the tube, wherein the tube, optionally, is formed of metal, wherein the tubing, optionally, is formed of polymer, and/or wherein the channel junction, optionally, is formed by a flow cell.

Paragraph E7. The detection system of any of paragraphs E1 to E6, further comprising one or more limitations of the detection system of any of paragraphs B1 to B24, C1 to C4, and G1.

Paragraph F1. A method of droplet detection, the method comprising: (a) moving a tube and a well relative to one another to create contact between an open end of the tube and an emulsion held by the well; (b) aspirating fluid of the emulsion from the well via the open end of the tube; (c) dispensing at least a portion of the aspirated fluid back into the well via the open end of the tube; (d) transporting droplets of the emulsion from the well, via the open end of the tube, and to a detection channel, after the steps of aspirating and dispensing; and (e) detecting a signal from droplets passing through the detection channel wherein, optionally, detecting a signal includes detecting light received from the detection channel and creating a signal representative of the detected light.

Paragraph F2. The method of paragraph F1, wherein the step of dispensing includes a step of dispensing more liquid into the well than was aspirated by the step of aspirating.

Paragraph F3. The method of paragraph F2, wherein the step of aspirating includes a step of aspirating a first volume of droplet-immiscible liquid, wherein the step of dispensing includes a step of dispensing a second volume of droplet-immiscible liquid, and wherein the second volume is greater than the first volume.

Paragraph F4. The method of any of paragraphs F1 to F3, wherein the steps of aspirating and dispensing are a first cycle of aspirating and dispensing, the method further comprising performing one or more additional cycles of aspirating and dispensing before the step of transporting droplets.

Paragraph F5. The method of any of paragraphs F1 to F4, wherein the step of dispensing including a step of dispensing fluid from the tube onto a portion of the emulsion remaining in the well, while the open end of the tube is vertically aligned with, and separated from, the portion of the emulsion, such that the dispensed fluid falls onto the portion of the emulsion.

Paragraph F6. The method of paragraph F5, wherein the step of dispensing has a shorter duration than the step of aspirating.

Paragraph F7. The method of any of paragraphs F1 to F6, wherein fluid enters the tube in the step of aspirating at a lower flow rate than fluid exits the tube in the step of dispensing.

Paragraph F8. The method of any of paragraphs F1 to F7, wherein the step of detecting a signal includes a step of detecting light emitted from droplets.

Paragraph F9. The method of any of paragraphs F1 to F8, wherein the tube is in fluid communication with the detection channel during the steps of aspirating and dispensing.

Paragraph F10. The method of any of paragraphs F1 to F9, wherein the emulsion includes a liquid continuous phase, and wherein the step of aspirating fluid includes a step of selectively aspirating the liquid continuous phase relative to the droplets.

Paragraph F11. The method of paragraph F10, wherein the droplets form a pack due to a density difference between the droplets and the continuous phase, and wherein the step of aspirating is performed, at least in part, while the open end of the tube is located in a substantially droplet-free volume portion of the continuous phase located below or above the pack.

Paragraph F12. The method of paragraph F10, wherein the step of aspirating includes a step of aspirating droplets of the emulsion.

Paragraph F13. The method of paragraph F12, wherein the droplets are selectively aspirated towards an end of the step of aspirating.

Paragraph F14. The method of any of paragraphs F1 to F13, wherein the tube has a uniform outer diameter.

Paragraph F15. The method of any of paragraphs F1 to F14, wherein individual droplets are surrounded by a proteinaceous skin.

Paragraph F16. The method of any of paragraphs F1 to F15, wherein the step of moving includes a step of piercing a sealing member over the well with the tube to access the well.

Paragraph F17. The method of any of paragraphs F1 to F16, wherein the open end of the tube is closer to a bottom of the well for the step of aspirating than the step of dispensing.

Paragraph F18. The method of any of paragraphs F1 to F17, wherein a vertical distance between the open end of the tube and a bottom of the well is changed as fluid is aspirated in the step of aspirating and/or as fluid is dispensed during the step of dispensing.

Paragraph F19. The method of any of paragraphs F1 to F18, wherein the step of aspirating transports fewer than one-half of the droplets of the emulsion into the tube through the open end thereof.

Paragraph F20. The method of any of paragraphs F1 to F19, wherein the step of dispensing disaggregates droplets of the emulsion.

Paragraph F21. The method of any of paragraphs F1 to F20, wherein the method is performed with the detection system of any of paragraphs B1 to B25, C1 to C4, E1 to E6, and G1.

Paragraph F22. The method of any of paragraphs F1 to 21 wherein the method further comprises any step(s) of the method of any of paragraphs A1 to A17 and D1 to D17.

Paragraph G1. A system for droplet detection, comprising: (a) a well to hold an emulsion; (b) a tube having an open end; (c) a detection channel; (d) a detector configured to receive and detect light from the detection channel; (e) one or more sources of positive/negative pressure each operatively connected to the tube and/or the detection channel; (f) a conveyor configured to move the well and the open end of the tube relative to one another; and (g) a processor configured to operate the conveyor, the one or more sources of positive/negative pressure, and the detector to (i) create contact between an open end of the tube and the emulsion held by the well, (ii) aspirate fluid of the emulsion from the well via the open end of the tube, (iii) dispense at least a portion of the aspirated fluid back into the well via the open end of the tube to disaggregate droplets of the emulsion, (iv) transport droplets of the emulsion from the well, via the open end of the tube, and to the detection channel, and (v) detect a signal from droplets passing through the detection channel wherein, optionally, the signal is detected by detecting light received from the detection channel and creating a signal representative of the detected light.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated. Finally, the present disclosure incorporates material by reference. If any ambiguity or conflict in the meaning of a term results from this incorporation by reference, the literal contents of the application govern construction of the term.

We claim:

1. A method of droplet detection, the method comprising:
providing a microfluidic device including a flow cell defining a plane and a channel network, the channel network including a sample inlet channel, at least one spacing-fluid inlet channel, and a spacing channel that are fluidically connected to one another at a channel junction, the channel network also including a detection channel, wherein the spacing channel has a first end fluidically connected to the channel junction and a second end fluidically connected to the detection channel;
driving a spacing fluid, and a plurality of droplets in a carrier liquid, through the channel network of the flow cell using one or more positive/negative pressure sources, wherein driving (a) aligns the plurality of droplets with one another in the sample inlet channel to generate a single-file droplet stream of the plurality of droplets in the carrier liquid entering the channel junction, (b) adds the spacing fluid to the single-file droplet stream in the carrier liquid at a location in the spacing channel where a cross-sectional area of a portion of a length of the spacing channel is decreasing towards the detecting channel, and (c) passes the single-file droplet stream through the spacing channel and the detection channel:
irradiating the plurality of droplets in the detection channel using a light source; and
detecting a signal from the irradiated plurality of droplets using a detector.

2. The method of claim 1, wherein driving includes passing the plurality of droplets through a tapered region of the sample inlet channel to align droplets of the plurality of droplets with one another.

3. The method of claim 1, wherein a velocity of spacing fluid entering the channel junction and a velocity of the plurality of droplets entering the channel junction are the same.

4. The method of claim 2, wherein the tapered region of the sample inlet channel defines a central axis and has an angle of taper with respect to the central axis of less than 10 degrees.

5. The method of claim 1, wherein driving includes applying suction to the channel network downstream of the detection channel using a negative pressure source of the one or more positive/negative pressure sources.

6. The method of claim 1, wherein the flow cell has a planar upper side opposite a planar lower side, and wherein the channel network is located between the planar upper side and the planar lower side of the flow cell.

7. The method of claim 1, wherein at least a portion of the spacing channel tapers toward the detection channel with a progressively decreasing angle of taper, wherein the at least a portion of the spacing channel has a length measured along a long axis of the spacing channel and has a maximum width measured perpendicular to the long axis and parallel to the plane, and wherein the length is greater than the maximum width.

8. The method of claim 7, wherein the length of the at least a portion of the spacing channel is at least ten times a minimum width of the at least a portion of the spacing channel measured parallel to the plane.

9. The method of claim 8, wherein the maximum width is at least three times the minimum width of the at least a portion of the spacing channel.

10. The method of claim 7, wherein the at least a portion of the spacing channel has a constant depth measured perpendicular to the plane.

11. The method of claim 7, wherein the at least one spacing-fluid inlet channel includes a pair of spacing-fluid inlet channels defining respective long axes that form an angle of less than 50 degrees with one another.

12. The method of claim 2, wherein the tapered region of the sample inlet channel has a length and a minimum width each measured parallel to the plane, and wherein the length of the tapered region of the sample inlet channel is at least ten times the minimum width.

13. The method of claim 7, wherein the length is at least three times the maximum width of the at least a portion of the spacing channel.

* * * * *